(12) United States Patent
Jones et al.

(10) Patent No.: US 11,173,044 B1
(45) Date of Patent: Nov. 16, 2021

(54) EXPANDING ORTHOPEDIC IMPLANT

(71) Applicant: Zavation Medical Products, LLC, Flowood, MS (US)

(72) Inventors: Joseph Matthew Jones, Madison, MS (US); John Lawrence Walker, Madison, MS (US)

(73) Assignee: Zavation Medical Products, LLC, Flowood, MS (US)

( * ) Notice: Subject to any disclaimer, the term of this patent is extended or adjusted under 35 U.S.C. 154(b) by 0 days.

(21) Appl. No.: 17/235,587

(22) Filed: Apr. 20, 2021

(51) Int. Cl.
*A61F 2/44* (2006.01)
*A61F 2/46* (2006.01)
*A61F 2/30* (2006.01)
*A61F 2/28* (2006.01)

(52) U.S. Cl.
CPC .... *A61F 2/447* (2013.01); *A61F 2002/30266* (2013.01); *A61F 2002/30387* (2013.01); *A61F 2002/30398* (2013.01); *A61F 2002/30433* (2013.01); *A61F 2002/30579* (2013.01); *A61F 2002/30772* (2013.01)

(58) Field of Classification Search
CPC ............ A61F 2/447; A61F 2002/30266; A61F 2002/30387; A61F 2002/30398; A61F 2002/30433; A61F 2002/30579; A61F 2002/30772
USPC ........................................... 623/17.11–17.16
See application file for complete search history.

(56) References Cited

U.S. PATENT DOCUMENTS

| | | | |
|---|---|---|---|
| 6,176,882 B1 | 1/2001 | Biedermann et al. | |
| 6,500,205 B1 | 12/2002 | Michelson | |
| 7,128,760 B2 | 10/2006 | Michelson | |
| 7,655,046 B2 | 2/2010 | Dryer et al. | |
| 7,850,733 B2 | 12/2010 | Baynham et al. | |
| 8,062,375 B2 | 11/2011 | Glerum et al. | |
| 8,105,382 B2 * | 1/2012 | Olmos ................ | A61F 2/4611 623/17.15 |
| 8,241,360 B2 | 8/2012 | Bao et al. | |
| 8,535,380 B2 | 9/2013 | Greenhalgh et al. | |
| 8,679,183 B2 | 3/2014 | Glerum et al. | |
| 8,894,712 B2 | 11/2014 | Varela | |
| 9,155,628 B2 | 10/2015 | Glerum et al. | |
| 9,233,007 B2 | 1/2016 | Sungarian et al. | |

(Continued)

FOREIGN PATENT DOCUMENTS

WO 2016178078 A1 11/2016

OTHER PUBLICATIONS

Notice of Allowance issued by USPTO for U.S. Appl. No. 16/135,734 dated Feb. 25, 2019.

*Primary Examiner* — Jessica Weiss
(74) *Attorney, Agent, or Firm* — IP & T Group LLP

(57) ABSTRACT

An expandable intervertebral implant having an upper body portion, a lower body portion opposite the upper body portion, a wedge member connecting the upper body portion to the lower body portion, a nose member having a tapered distal end and a proximal end opposite the distal end, and an actuator disposed between the nose member and the wedge member, for translation of the wedge member along a longitudinal axis of the implant. A pin connects to the actuator for positioning the nose member relative to the actuator. Translation of the wedge member along the longitudinal axis of the implant displaces the upper body portion and the lower body portion away from each other, thereby expanding the intervertebral implant.

20 Claims, 21 Drawing Sheets

(56) References Cited

U.S. PATENT DOCUMENTS

| | | | |
|---|---|---|---|
| 9,320,610 B2 | 4/2016 | Alheidt et al. | |
| 9,370,434 B2* | 6/2016 | Weiman | A61F 2/4455 |
| | | | 623/17.16 |
| 9,402,737 B2 | 8/2016 | Hawkins et al. | |
| 9,402,739 B2 | 8/2016 | Weiman et al. | |
| 9,414,936 B2 | 8/2016 | Miller et al. | |
| 9,492,288 B2 | 11/2016 | Wagner et al. | |
| 9,522,070 B2 | 12/2016 | Flower et al. | |
| 9,526,627 B2 | 12/2016 | Tabor et al. | |
| 9,539,108 B2 | 1/2017 | Glerum et al. | |
| 9,585,766 B2 | 3/2017 | Robinson | |
| 9,717,601 B2 | 8/2017 | Miller | |
| 9,717,605 B2 | 8/2017 | Baynham | |
| 9,757,249 B2 | 9/2017 | Radcliffe et al. | |
| 9,770,343 B2 | 9/2017 | Weiman | |
| 9,782,265 B2 | 10/2017 | Weiman et al. | |
| 9,782,271 B2 | 10/2017 | Cipoletti et al. | |
| 9,788,971 B1 | 10/2017 | Stein | |
| 9,801,733 B2 | 10/2017 | Wolters et al. | |
| 9,801,734 B1 | 10/2017 | Stein et al. | |
| 10,278,830 B1* | 5/2019 | Walker | A61F 2/4455 |
| | | | 623/17.16 |
| 10,350,081 B2* | 7/2019 | Seifert | A61F 2/4455 |
| | | | 623/17.16 |
| 10,383,741 B2 | 8/2019 | Butler et al. | |
| 10,492,924 B2 | 12/2019 | Stein et al. | |
| 2011/0093074 A1* | 4/2011 | Glerum | A61F 2/4611 |
| | | | 623/17.16 |
| 2011/0319997 A1 | 12/2011 | Glerum et al. | |
| 2012/0265309 A1 | 10/2012 | Glerum et al. | |
| 2013/0023994 A1* | 1/2013 | Glerum | A61F 2/4611 |
| | | | 623/17.16 |
| 2013/0158669 A1 | 6/2013 | Sungarian et al. | |
| 2014/0067071 A1 | 3/2014 | Weiman et al. | |
| 2014/0180421 A1* | 6/2014 | Glerum | A61F 2/30771 |
| | | | 623/17.16 |
| 2016/0045328 A1 | 2/2016 | Matthews et al. | |
| 2016/0081814 A1* | 3/2016 | Baynham | A61F 2/447 |
| | | | 623/17.16 |
| 2016/0151168 A1* | 6/2016 | Weiman | A61F 2/4455 |
| | | | 623/17.16 |
| 2016/0256291 A1 | 9/2016 | Miller | |
| 2017/0056197 A1* | 3/2017 | Weiman | A61F 2/4611 |
| | | | 623/17.16 |
| 2017/0258605 A1 | 9/2017 | Blain et al. | |
| 2020/0297507 A1 | 9/2020 | Iott et al. | |

* cited by examiner

EXPANDING ORTHOPEDIC IMPLANT

CROSS REFERENCE TO RELATED APPLICATIONS

This application is related to U.S. Ser. No. 16/135,734, now U.S. Pat. No. 10,278,830, entitled "Expandable Orthopedic Implant," the entire contents of which are incorporated herein by reference.

BACKGROUND OF THE INVENTION

Field of the Invention

The present invention relates to implant devices for treating in particular spinal disorders.

Description of the Related Art

Disorders of the spine often result in degeneration of the spinal disc in the intervertebral space between the vertebral bodies. Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Conservative treatment can include non-operative treatment requiring patients to adjust their lifestyles and submit to pain relievers and a level of underlying pain. Operative treatment options include disc removal or the fusion or fixation of vertebrae together. Adjacent vertebra can be fixated or fused to each other using devices or bone grafts. These may include, for example, screw and rod systems, interbody spacers threaded fusion cages and the like.

Some fixation or fusion devices are attached to the vertebra from the posterior side. The device will protrude and result in additional length (i.e., needed to overlap the vertebrae) and additional hardware to separately attach to each vertebrae. Fusion cages and allografts are contained within the intervertebral space, but are inserted into the intervertebral space in the same dimensions as desired to occupy the intervertebral space. This requires that an opening sufficient to allow the cage or graft to be inserted into the intervertebral space.

In the field of medical implant devices, implant devices are often implanted into an intervertebral disc space in a collapsed state and expanded to a desired height. Expansion has been accomplished by translating an expansion mechanism mated to the inferior and superior endplates. In addition, a large aperture at the proximal end of the device allows for post packing of bone graft material into the hollow interior of the device, which is in communication with a fusion aperture in each of the superior and inferior endplates.

To achieve expansion and contraction the endplates are typically fixed in the longitudinal direction during translation of the expansion mechanism. An endplate retainer can be housed within the distal end of the housing mates with both the superior and inferior endplates and prohibits translation of the endplates, but allows for expansion.

U.S. Pat. No. 6,500,205 (the entire contents of which are incorporated herein by reference) describes a threaded implant having arcuate portions of upper and lower members that in a first, collapsed, or insertion position are parallel to one another and form at least a portion of a cylinder along a substantial portion of the length of the implant.

U.S. Pat. No. 7,128,760 (the entire contents of which are incorporated herein by reference) describes interbody spinal fusion implants being at least in part radially expandable at one of the leading or trailing ends to expand both the height and at least a portion of the width of the implants.

U.S. Pat. No. 7,655,046 (the entire contents of which are incorporated herein by reference) describes an expandable spinal implant comprising a cage body including at least two movable branches having first end portions that are interconnected to one another and second end portions that are movable relative to one another. An expansion member in the '046 patent co-acts with first and second shell portions to transition the cage body to an expanded configuration as the expansion member is axially displaced along said first and second pairs of longitudinal edges.

U.S. Pat. No. 8,241,360 (the entire contents of which are incorporated herein by reference) describes an artificial disc device for replacing a damaged nucleus in which the device may be inserted into the natural annulus in a collapsed or compressed state or arrangement and then may be expanded within and retained by the annulus therein.

U.S. Pat. No. 8,535,380 (the entire contents of which are incorporated herein by reference) describes an implantable orthopedic stability device. The device had a contracted and an expanded configuration which could support and be fixed to either or both of adjacent vertebrae.

U.S. Pat. No. 8,894,712 (the entire contents of which are incorporated herein by reference) describes an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member from the inferior member.

U.S. Pat. No. 8,679,183 (the entire contents of which are incorporated herein by reference) describes an expandable fusion device capable of being installed inside an intervertebral disc space to maintain normal disc spacing and restore spinal stability. In the '183 patent, the fusion device includes a body portion, a first endplate, and a second endplate, the first and second endplates capable of being moved in a direction away from the body portion into an expanded configuration or capable of being moved towards the body portion into an unexpanded configuration.

U.S. Pat. No. 9,320,610 (the entire contents of which are incorporated herein by reference) describes an expandable implant including top and bottom plates having angled inner surface that interact with expansion members. The expansion members were situated on an actuator and included at least one vertical projection for interacting with a recess in the plates.

U.S. Pat. No. 9,414,936 (the entire contents of which are incorporated herein by reference) describes an intervertebral implant comprising a first component and a second component. The second component included an actuator and a third component comprises a first ramp and a second ramp axially spaced apart from the first ramp. The third component comprised rails including at least a portion of the ramps. The actuator was engageable with the third component to effect axial translation such that the ramps engage at least one of the components between a first configuration and a second configuration.

U.S. Pat. No. 9,526,627 (the entire contents of which are incorporated herein by reference) describes an intervertebral implant to be implanted within an intervertebral space between endplates of adjacent vertebra during use. The implant of the '627 patent included an upper member having an inferior surface including an upper guide track and a superior surface to contact an endplate of an upper one of the adjacent vertebra during use, a lower member having a superior surface including a lower guide track and an inferior surface to contact an endplate of a lower one of the adjacent vertebra during use, and an insert having a superior surface including an upper guide rail to engage the upper guide track during use and an inferior surface including a lower guide rail to engage the lower guide track during use.

U.S. Pat. No. 9,717,601 (the entire contents of which are incorporated herein by reference) describes an implant including a first plate and a second plate, a first wedge member and a second wedge member spaced from the first wedge member that couple the first and second plates together. In the '601 patent, the first and second wedge members were configured to translate along the first and second plates from a first contracted configuration into a second separated configuration. The implant included an actuation member coupled to the first wedge member and the second wedge member. The actuation member was configured to move the first and second wedge members from the first contracted configuration into the second separated configuration so that the first and second plates separate from each other.

U.S. Pat. No. 9,717,605 (the entire contents of which are incorporated herein by reference) describes a spinal fusion device that is expandable. The spinal fusion device of the '605 patent features a top and bottom surface for engaging adjacent vertebrae, a hollow center for stacking of bone or bone growth material, and a slidable mechanism with grooves for expanding or un-expanding the device.

U.S. Pat. No. 9,770,343 (the entire contents of which are incorporated herein by reference) describes a spacer for separating bones of a joint, the spacer includes a frame having a longitudinal axis, and ramped surfaces. In the '343 patent, an endplate configured to engage a bone of the joint had ramped surfaces mateable with the ramped surfaces of the frame. When the endplate was moved relative to the frame in a direction along the longitudinal axis of the frame, the endplate was moved in a direction away from the frame to increase the height of the spacer.

U.S. Pat. No. 9,788,971 (the entire contents of which are incorporated herein by reference) describes an expandable spinal fusion implant comprising first and second endplates coupled to an expansion member that sits within a housing. The expansion member was translated by a drive mechanism, whereby translation of the expansion member by the drive mechanism in a distal and proximal directions caused the distance between the endplates to increase and decrease, respectively.

U.S. Pat. No. 10,350,081 (the entire contents of which are incorporated herein by reference) describes an orthopedic device for a patient comprising: a spacer comprising: a body member; a translation member received in the body member, the translation member including at least one upper ramp portion and one lower ramp portion; an upper endplate having an upper contact surface for engaging a first vertebra and at least one lower ramp for engaging the upper ramp portion of the translation member, wherein the upper endplate includes an upper plate portion comprising a bottom post; a lower endplate having a lower contact surface for engaging a second vertebra and at least one upper ramp for engaging the lower ramp portion of the translation member. In the '081 patent, a polyetheretherketone (PEEK) washer disposed in between an interface of the translation member and an actuation member was used to prevent metal-on-metal contact.

U.S. Pat. No. 10,383,741 (the entire contents of which are incorporated herein by reference) describes an expandable implant including a top support assembly defining an upper surface configured to engage a first portion of vertebral bone; a bottom support assembly defining a lower surface configured to engage a second portion of vertebral bone; and a control assembly coupled to the top support assembly and the bottom support assembly and configured to control relative movement between the top support assembly and the bottom support assembly between a collapsed position and an expanded position. In the collapsed position, the upper surface is generally parallel to the lower surface, and in the expanded position, a portion of the upper surface extends at an acute angle relative to a portion of the lower surface.

U.S. Pat. No. 10,492,924 (the entire contents of which are incorporated herein by reference) describes an expandable spinal fusion implant including a housing, upper and lower endplates, a wedge positioned within the housing and between the upper and lower endplates and a drive mechanism to urge the wedge distally between the upper and lower endplates to increase the separation between the endplates and expand the overall height of the distal end of the implant.

U.S. Pat. No. 2020/0297507 (the entire contents of which are incorporated herein by reference) describes a joint spacer for therapeutically maintaining a separation of bones of a joint. The joint spacer comprises a frame having distal and proximal ends defining a longitudinal axis extending therebetween, a carriage slideably retained within the frame, an actuator screw threadably engaged with the frame, hereby when the carriage is slideably moveable by rotation of the actuator screw, an endplate ramped surface slides against a carriage ramped surface to cause the endplate to move along an axis transverse to the longitudinal axis to increase a height of the spacer.

SUMMARY OF THE INVENTION

In one embodiment, there is provided an expandable intervertebral implant comprising an upper body portion, a lower body portion opposite the upper body portion, a wedge member connecting the upper body portion to the lower body portion, a nose member having a tapered distal end and a proximal end opposite the distal end, the nose member slidably connected to the upper body portion and the lower body portion, an actuator disposed between the nose member and the wedge member, for translation of the wedge member along a longitudinal axis of the implant, the actuator on a first side slidably connected the nose member and on a second side threadably connected to the wedge member, a pin connects to the actuator for positioning the nose member relative to the actuator; and a frictional bearing contacting the actuator and providing a frictional force retarding movement of the upper body portion relative to the lower body portion.

In one embodiment, there is provided an expandable intervertebral implant comprising an upper body portion, a lower body portion opposite the upper body portion, a wedge member extending along a longitudinal axis of the implant and connecting the upper body portion to the lower body portion, a nose member having a tapered distal end and a proximal end opposite the distal end, an actuator disposed offset from the longitudinal axis and disposed between the nose member and the wedge member, for translation of the wedge member along a longitudinal axis of the implant, wherein a series of dovetail grooves connect the upper body portion, the lower body portion, the wedge member, and the nose member together, and translation of the wedge member along the longitudinal axis of the implant displaces the upper body portion and the lower body portion away from each other, thereby expanding the intervertebral implant.

In one embodiment, there is provided an expandable intervertebral implant comprising an upper body portion having an asymmetric graft window with a larger opening to an anterior side of the implant than to a posterior side of the implant, a lower body portion opposite the upper body portion, a wedge member connecting the upper body portion to the lower body portion, the wedge member comprises in order a first wedge, a second wedge, and a third wedge connected together by a rail, a nose member having a tapered distal end and a proximal end opposite the distal end, an actuator disposed between the nose member and the wedge member, for translation of the wedge member along a longitudinal axis of the implant, wherein a series of dovetail grooves connect the upper body portion, the lower body portion, the wedge member, and the nose member together, and translation of the wedge member along the longitudinal axis of the implant displaces the upper body portion and the lower body portion away from each other, thereby expanding the intervertebral implant.

In one embodiment, there is provided a system for stabilization of vertebra, comprising the expandable implant(s) described above; and an insertion tool which turns the actuator described above and thereby expands the implant.

In one embodiment, there is provided a method for stabilization of vertebra, comprising attaching an insertion tool to the expandable implant(s) described above, inserting the expandable implant into an intervertebral space between adjacent vertebra; and expanding the expandable implant.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein:

FIG. 4E-1 is a schematic of a sectional view of the frictional bearing element of FIG. 4E:

FIG. 8A-1 is a schematic depiction of another implant of the present invention:

FIG. 8A-2 is a schematic depiction of the implant shown in FIG. 8A-1 in a collapsed state;

FIG. 8A-3 is a schematic depiction of the implant shown in FIG. 8A-1 in an expanded state;

FIG. 8E-1 is a schematic depiction of another aspect of the implant shown in FIG. 8A;

FIG. 8E-2 is a schematic depiction of the upper body portion showing dovetails for engagement with dovetail grooves on the wedge member;

DETAILED DESCRIPTION OF THE INVENTION

The implants of this invention are designed for spinal fusion procedures to be used with autogenous bone graft in skeletally mature patients. While this invention is not so limited, the implants in one embodiment are intended for use at either one level or two contiguous levels in the lumbar spine, from L2 to S1, for the treatment of degenerative disc disease (DDD) with up to Grade I spondylolisthesis. DDD is defined herein as back pain of discogenic origin with degeneration of the disc confirmed by history and radiographic studies.

Expandable Implants

In one embodiment of the invention, the implants constitute expandable posterior lumbar interbody fusion (PLIF) implant products, although this invention is not limited to this specific target use.

Figure 2:
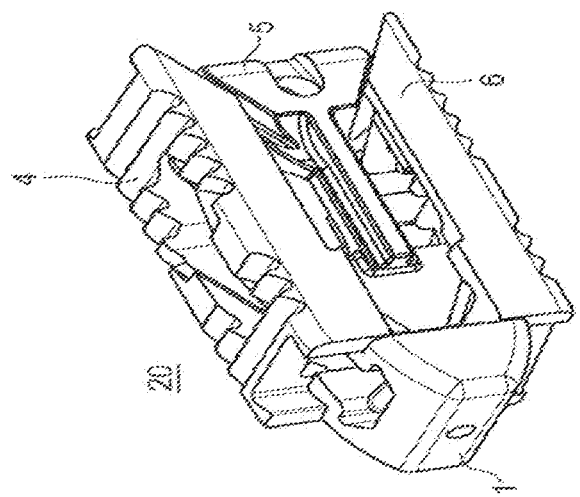
FIG. 2 is a perspective view of the implant device of the invention in an expanded state.
Figure 1:
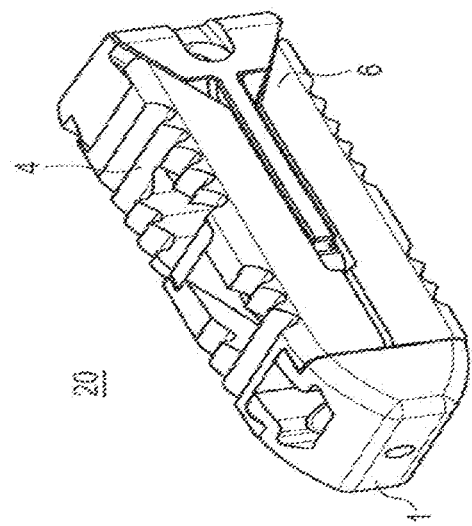
FIG. 1 is a perspective view of the implant device of the invention in a collapsed state.

With reference to FIGS. 1 and 2. FIG. 1 is a perspective view of the expandable intervertebral implant 20 in a collapsed state. FIG. 2 is a perspective view of the expandable intervertebral implant 20 in an expanded state. In one embodiment of the invention, the expandable intervertebral implant 20 has a nose member 1 having a tapered distal end and a proximal end opposite the distal end. A pin 2 (not shown in this perspective) is disposed in a center of the nose member 1 and connects to an actuator 3 (not shown in this perspective) for centering the nose member 1 with the actuator 3. The pin 2 maintains a position of the nose member 1 centered to the actuator 3 once the implant has been assembled. An upper body portion 4, a wedge member 5, a lower body portion 6 opposite the upper body portion are shown in FIGS. 1 and 2. The wedge member 5 connects the upper body portion 4 to the lower body portion 5.

Figure 3:
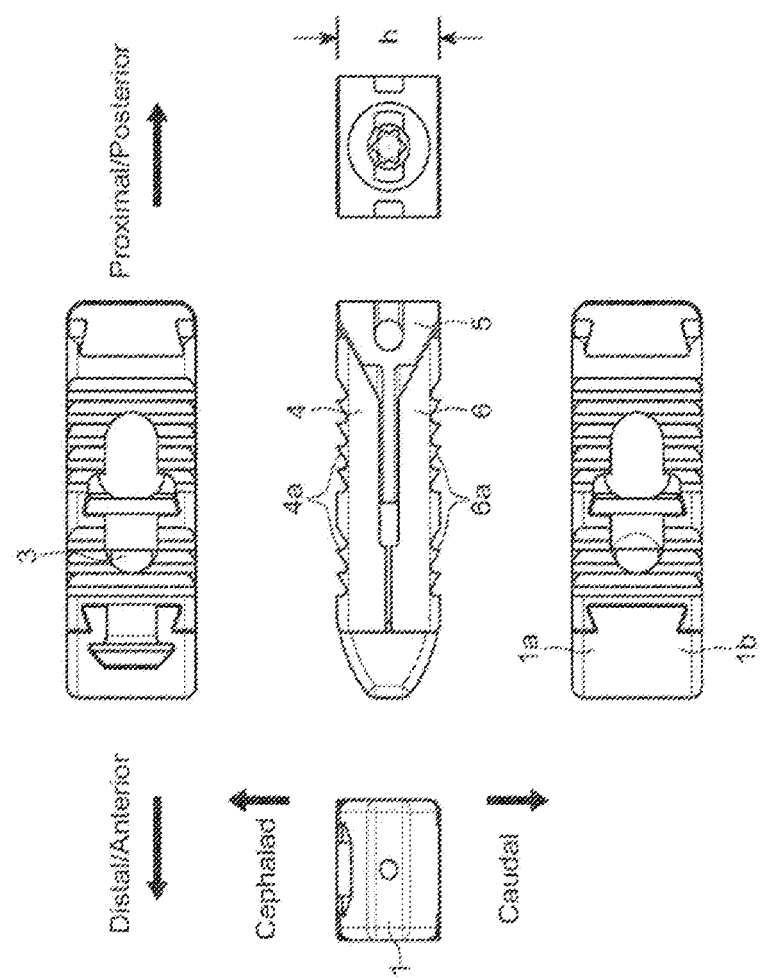
FIG. 3 is a composite drawing showing a top down exploded view, a frontal, side, and rear view, and a bottom view of the implant device of the invention.

Translation of the wedge member 5 along the longitudinal axis of the implant, e.g., by turning of the actuator 3, displaces the upper body portion 4 and the lower body portion 6 away from the wedge member 5 and away from each other, thereby expanding the intervertebral implant for example in the cephalad direction denoted in FIG. 3.

FIG. 3 is a composite drawing showing a top-down exploded view, a frontal, side, and rear view, and a bottom view of the implant of the invention. As evident from FIG. 3, at least one of the upper body portion 4 and the lower body portion 6 comprises a corrugated surface 4*a* or 6*a* for engaging with vertebra. The upper body portion 4 and the lower body portion 6 provide the load bearing surfaces for the intervertebral loads once implant 20 has been implanted and expanded. As evident from FIG. 3, in one embodiment of the invention, the nose member 5 is slidably connected to the upper body portion 4 and is slidably connected to the lower body portion 5 by the exterior dovetail grooves 1*a*, 1*b* on nose member 1.

Figure 4A:
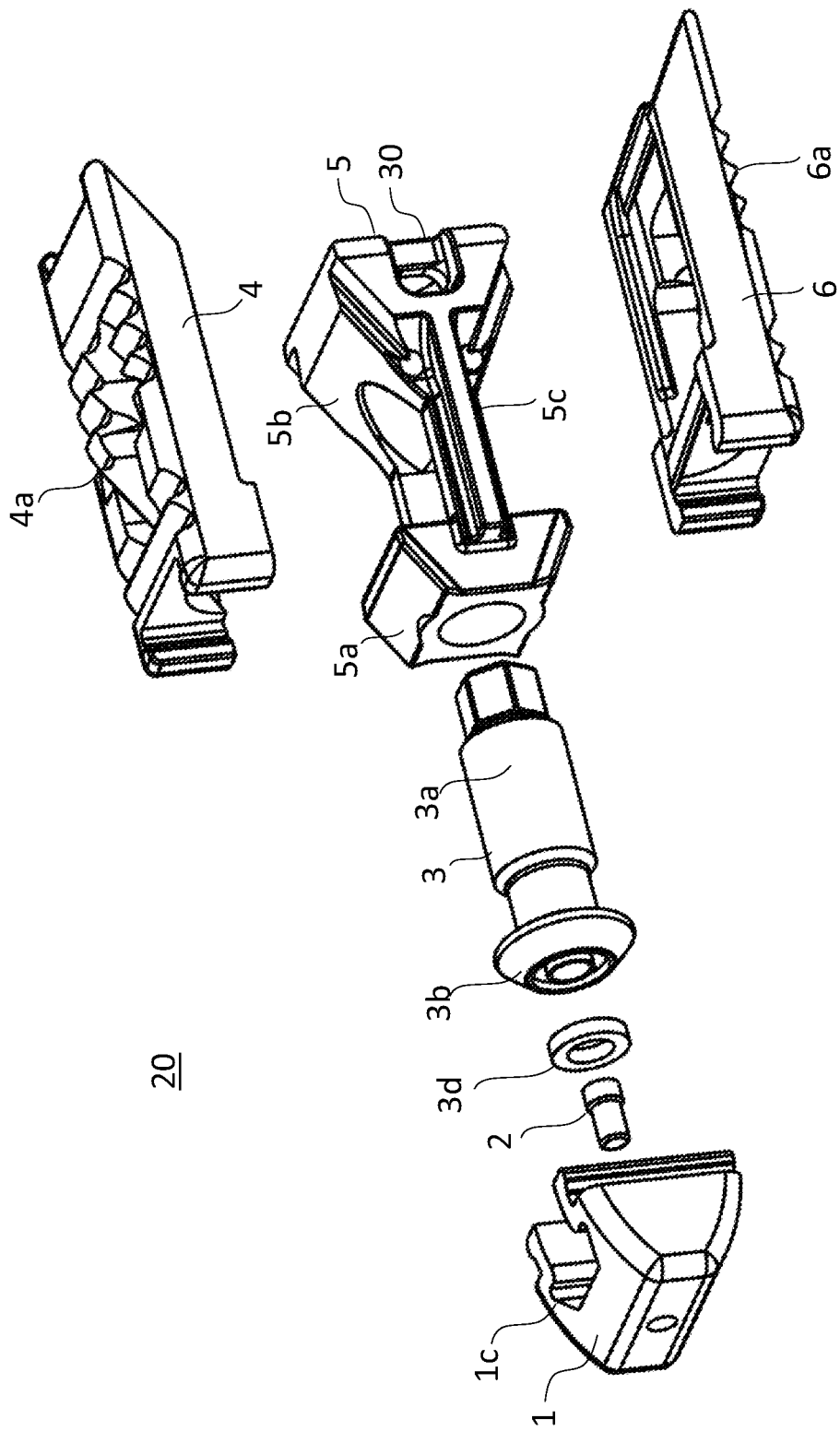
FIG. 4A is a schematic depiction of the individual components of the implant device, showing the relative positions of those components.

FIG. 4A is a schematic depiction of the individual components of the implant 20, showing the relative positions of those components. As evident from FIGS. 3 and 4, actuator 3 is disposed between nose member 1 and wedge member 5. In one embodiment of the invention, the wedge member comprises a first wedge 5*a* and a second wedge 5*b* connected together by one or more rails 5*c*. With reference to FIG. 4A, nose member 1 centers by way of pin 2 and retains the head of actuator 3 during expansion of implant 20.

Figure 4B:
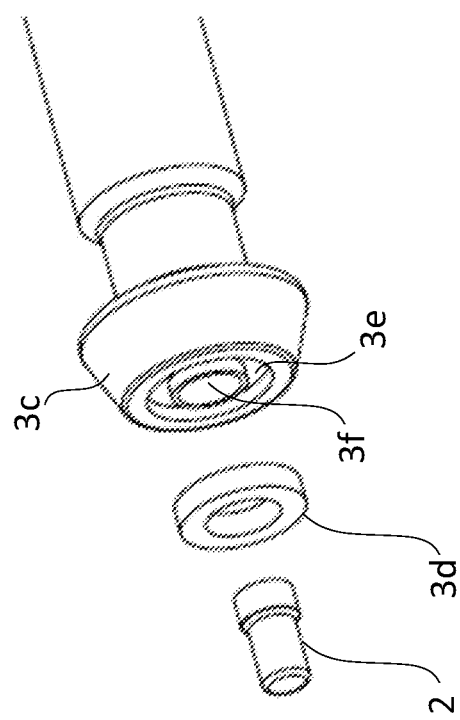
FIG. 4B is an expanded view of the front of the actuator of the present invention showing one frictional bearing construction of the invention.

FIG. 4B is an expanded view of the head 3*b* of the actuator 3 having a flange 3*c* which retains washer 3*d* into recess 3*e*. Washer 3*d* can be made from similar or dissimilar materials as the actuator, and in one example, washer 3*d* is made from polyetheretherketone (PEEK). Washer 3*d* is merely one example of a frictional bearing that provides a frictional force retarding movement of the upper body portion relative to the lower body portion. As shown in FIG. 4B, pin 2 fits into a reception hole 3*f* disposed on a central axis of the actuator 3. While the circular and symmetric geometry shown in FIG. 4A is preferred, the washer and its recess need not be circular and split washers and spacers could be placed on the flange in asymmetric patterns.

Regardless of the material that washer 3*d* is made of, washer 3*d* serves multiple purposes in the present invention. In one embodiment, compression of washer 3*d* in the interface between nose member 2 and actuator 3 provides friction. This friction helps keep the parts centered and prevents binding of the components during expansion/contraction. The friction also provides additional resistance to post operation collapse of the cage.

During assembly, pin 2 is pressed into the nose member 1 with a portion of pin 2 extending beyond the distal end of nose member 1. The upper body portion 4 and the lower body portion 6 are coupled to wedge member 5 along respective dovetails and dovetail groove with full engagement into a collapsed or non-expanded state. Actuator 3 is threaded into the wedge member 5. The head position of actuator 3 is adjusted so that it is aligned with the mating slot in nose member 1, while the vertical dovetails of the endplates are aligned with their mating dovetail grooves in nose member 1. Next, washer 3*d* is placed in recess 3*e* on flange 3*c* of the actuator. Then, the head of actuator 3 (with washer 3*d* in place) is slid into groove 1*c* of nose member 1, compressing washer 3*d* in the process to provide the friction noted above. Once the nose member 1 is close to alignment, pin 2 is pushed through an opening in the washer 3*d* into reception hole 3*f* of actuator 3. The part of pin 2 which formerly was protruding from the distal tip of nose member 1 is now flush with the distal tip of nose member 1.

In one embodiment of the invention, the frictional bearing can be a wave spring applying an axial force on the head of the actuator. In another embodiment of the invention, the frictional bearing can be a spring loaded cap to apply an axial force on the head of the actuator. In still another embodiment, the frictional bearing can be a PEEK pellet (or pin) inserted in the nose piece and oriented to interfere with the head of the actuator, and thereby apply an axial force on the head of the actuator.

Figure 4C:
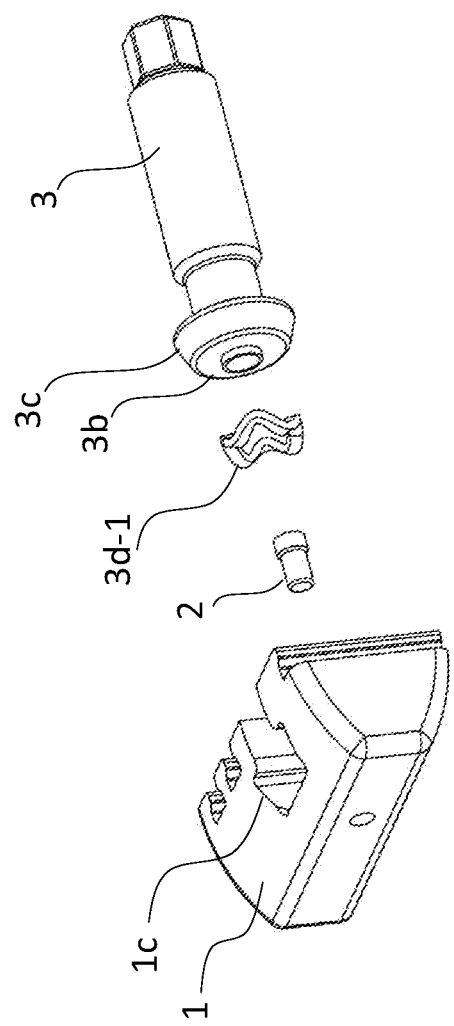
FIG. 4C is a schematic depiction of another frictional bearing element of the invention.
Figure 4D:
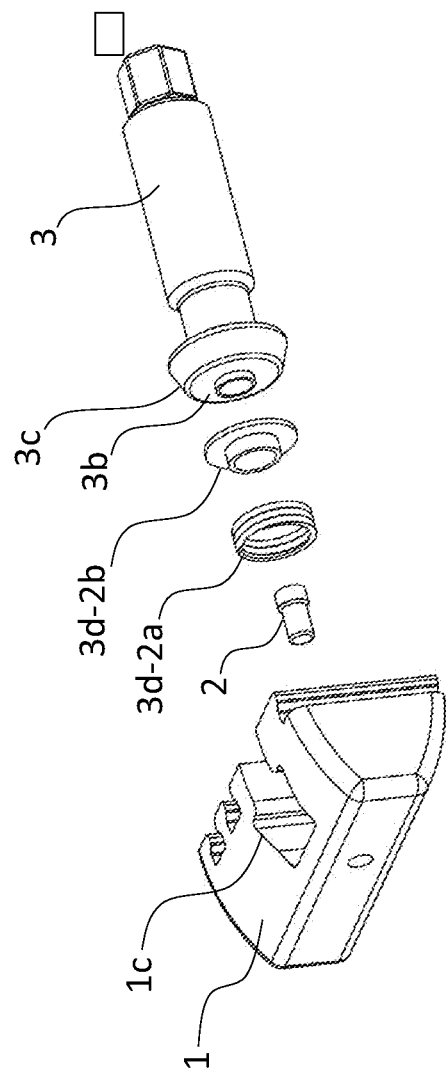
FIG. 4D is a schematic depiction of another frictional bearing element of the invention.
Figure 4E:
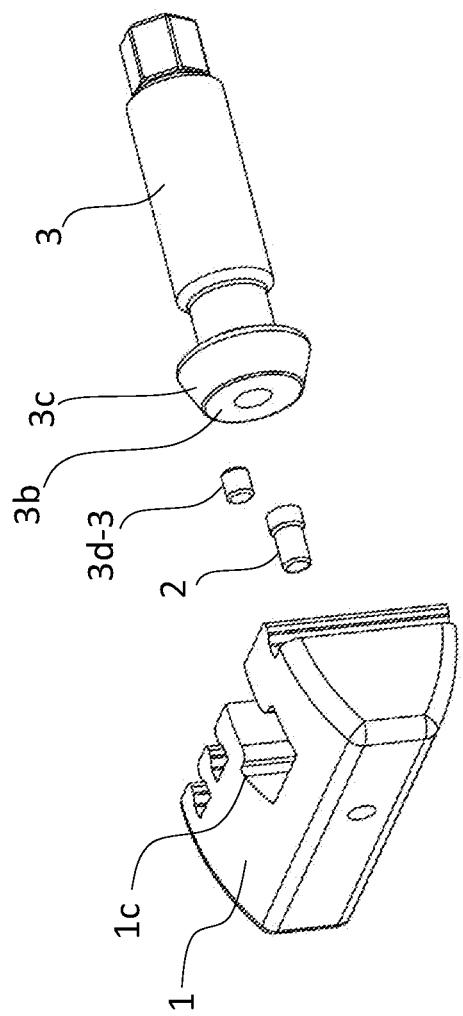
FIG. 4E is a schematic depiction of another frictional bearing element of the invention.
Figures 1, 4E:
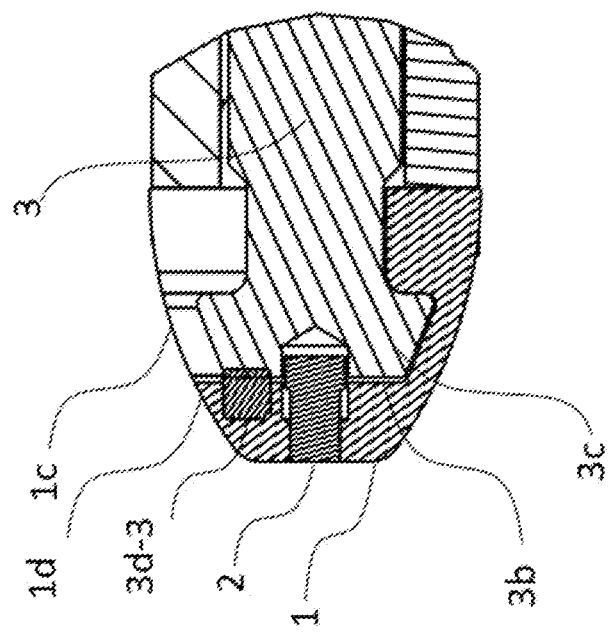

These latter embodiments are shown respectively in FIGS. 4C, 4D, and 4E.

In particular. FIG. 4C shows a wave spring 3*d*-1 for application of an axial force to head 3*b* of the actuator 3. In this embodiment, there is no need to have recess 3*e* on head 3*b* of the actuator 3 (as shown in FIG. 4B) although such a recess may be provided. In this embodiment, during assembly, pin 2 is pressed into the nose member 1 with a portion of pin 2 extending beyond the distal end of nose member 1. The upper body portion 4 and the lower body portion 6 are coupled to wedge member 5 along respective dovetails and dovetail groove with full engagement into a collapsed or non-expanded state. Actuator 3 is threaded into the wedge member 5. The head position of actuator 3 is adjusted so that it is aligned with the mating slot in nose member 1, while the vertical dovetails of the endplates are aligned with their mating dovetail grooves in nose member 1. Next, wave spring 3*d*-1 is placed on flange 3*c* of the actuator. Then, the head of actuator 3 (with wave spring 3*d*-1 in place) is slid into groove 1*c* of nose member 1, compressing wave spring 3*d*-1 in the process to provide friction.

In particular, FIG. 4D shows a spring loaded cap for application of an axial force to head 3*b* of the actuator 3. In this embodiment, spring loaded cap 3*d*-2*a* is axially compressed against mating flange 3*d*-2*b* to provide an axial force on the head 3*b* of the actuator 3. In this embodiment, during assembly, pin 2 is pressed into the nose member 1 with a portion of pin 2 extending beyond the distal end of nose member 1. The upper body portion 4 and the lower body portion 6 are coupled to wedge member 5 along respective dovetails and dovetail groove with full engagement into a collapsed or non-expanded state. Actuator 3 is threaded into the wedge member 5. The head position of actuator 3 is adjusted so that it is aligned with the mating slot in nose member 2, while the vertical dovetails of the endplates are aligned with their mating dovetail grooves in nose member 1. Next, spring loaded cap 3*d*-2*a* with the mating flange 3*d*-2*b* is placed on flange 3*c* of the actuator. Then, the head of actuator 3 (with spring loaded cap 3*d*-2*a* and the mating flange 3*d*-2*b* in place) is slid into groove 1*c* of nose member 1, compressing spring loaded cap 3*d*-2*a* in the process to provide friction.

In particular, FIG. 4E shows a PEEK pellet 3*d*-3 (or pin 3*d*-3) inserted in the nose member 1 and oriented to interfere with the head of the actuator for application of an axial force to head 3*b* of the actuator 3. In this embodiment, pin 3*d*-3 is axially compressed to provide an axial force on the head 3*b* of the actuator 3. In this embodiment, during assembly, pin 2 is pressed into the nose member 1 with a portion of pin 2 extending beyond the distal end of nose member 1. The upper body portion 4 and the lower body portion 6 are coupled to wedge member 5 along respective dovetails and dovetail groove with full engagement into a collapsed or non-expanded state. Actuator 3 is threaded into the wedge member 5. The head position of actuator 3 is adjusted so that it is aligned with the mating slot in nose member 1, while the vertical dovetails of the endplates are aligned with their mating dovetail grooves in nose member 1. Next, pin 3*d*-3 is inserted in a mating hole 1*d* in nose member 1 as shown in FIG. 4E-1 Thereafter, the head of actuator 3 is slid into groove 1*c* of nose member 1, and with pin 3*d*-3 in place, compresses pin 3*d*-3 to provide friction. The asymmetric placement of pin 3*d*-3 on one side of pin 2 also serves to assist in providing the frictional resistance.

In one embodiment of the present invention, regardless of the type of frictional bearing used, the frictional force prevents relative movement of the upper body portion 4 to the lower body portion 6. In one embodiment, the frictional force prevents collapse of the expandable implant under its own weight.

In one embodiment of the invention, the actuator is disposed closer to the nose member than to a posterior of the implant. In general, the inventive implant expands by utilizing actuator 3 which is connected by a threaded connection to wedge member 5, which contains for example a pair of wedges 5*a*, 5*b*. When rotated, actuator 3 pulls the wedges (as a set) closer to the nose member 1 of implant 20 and, in turn, drives the upper and lower body portions 4, 6 away from the centerline of implant 20. In other words, with actuator 3 being threadably connected to wedge member 5, rotating actuator 3 translates the wedge member 5 along the longitudinal axis of implant 20. Actuator 3 in one embodiment has a threaded outside surface 3*a* with a head 3*b* of the actuator, opposite the wedge member 5, closer to the nose member 1 than to the posterior of implant 20. In one embodiment, actuator 3 and wedge member 5 have respectively male and female threads to thereby advance wedge member 5 when the actuator 3 is turned.

As illustrated above, the present invention is an expandable (intervertebral) implant comprising an upper body portion 4, a lower body portion 6 opposite the upper body portion 4, a wedge member 5 connecting the upper body portion 4 to the lower body portion 6, a nose member 1 having a tapered distal end and a proximal end opposite the distal end, the nose member 1 slidably connected to the upper body portion 4 and the lower body portion 6, an actuator 3 disposed between the nose member 1 and the wedge member 5, for translation of the wedge 5 member along a longitudinal axis of the implant, the actuator 3 on a first side slidably connected the nose member 1 and on a second side threadably connected to the wedge member 5, and a pin 2 connects to the actuator 3 for positioning the nose member 1 relative to the actuator 3. In one embodiment, the expandable implant includes a frictional bearing providing a frictional force retarding movement of the upper body portion relative to the lower body portion. In one embodiment, toward a side of the actuator 3 coupled to the nose member 1, actuator 3 has a flange 3*c*, a reception hole 3*f* in the flange 3*c* disposed on a central axis of the actuator 3 for reception of the pin 2, and a washer 3*d* disposed on the flange (e.g., in recess 3*e*) and surrounding the reception hole 3*f*. In one embodiment of the invention, as noted above, after assembly of the implant, washer 3*d* is in a compressed state compressed between the actuator 3 and the nose member 1, thereby providing a frictional force retarding movement of upper body portion 4 relative to lower body portion 6. In one embodiment of the invention, washer 3*d* is in the compressed state comprises the aforementioned frictional bearing.

In one embodiment of the invention, the implants comprise low profile implants with a minimal insertion height h for insertion into a collapsed intervertebral disc space. In this aspect of the invention, the height of the implant is that of the wedge member height, as seen in FIG. 3, which constitutes the maximum expansion distance. Accordingly, in this aspect of the invention, back side of the second wedge comprises the posterior end of implant 20 and comprises an entire height of the implant. Once inserted (facilitated by its low profile in this embodiment), implant 20 can expand for example in the cephalad-caudal direction(s) to facilitate disc height restoration.

Figure 5:
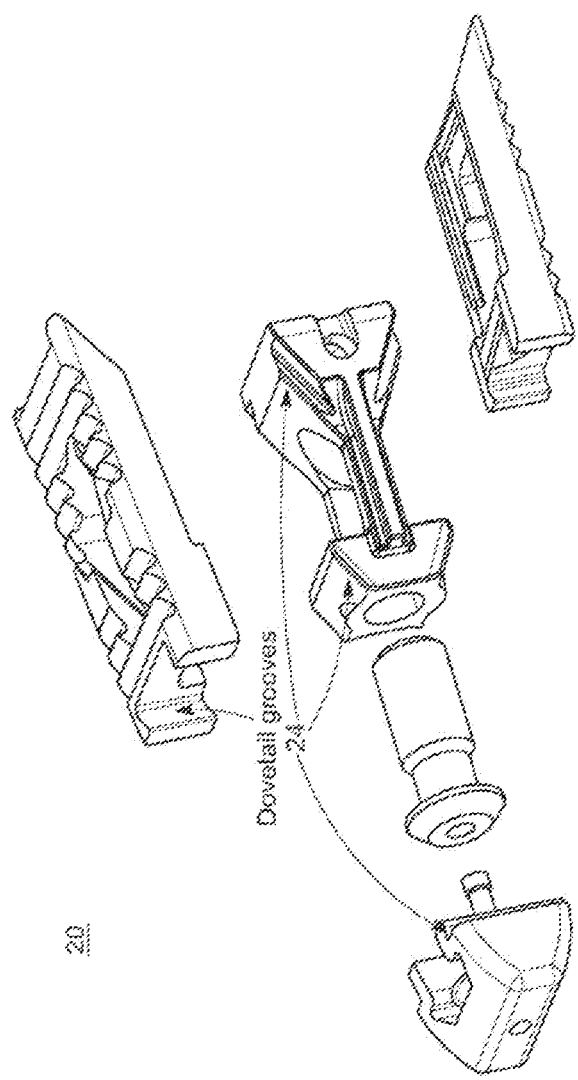
FIG. 5 is a schematic depiction of the individual components of the implant with attention on the dovetail groove assembly construction.

FIG. 5 is a schematic depiction of the individual components of the implant 20 with attention on the dovetail groove assembly construction. As seen in FIG. 5, nose member 1 uses dovetail grooves 24 to slidably connect and guide expansion of the upper and lower body portions 4, 6 and restrain any anterior-posterior movement of the upper and lower body portions 4, 6. Moreover, in one embodiment, dovetail grooves on the wedge member 5 hold and slidably connect the upper body portion 4 and the lower body portion 6 to the wedge member 5. In another embodiment, dovetail grooves hold and slidably connect the upper body portion 4 and the lower body portion 6 to the nose member 1. In another embodiment, a proximal end of nose member 1 comprises a pair of facing dovetail grooves 1*a*, 1*b* comprising respective slots to receive therein the head 3*a* of the actuator 3.

In still another embodiment, a series of dovetail grooves connect the nose member 1, the upper body portion 4, the wedge member 5, and the lower body portion 6 together. In still another embodiment, the nose member 1 slidably connects to the upper body portion 4 and the lower body portion 6 by a set of dovetail groove on an external surface of the nose member 1. In still another embodiment, a set of dovetail grooves on the first wedge 5*a* and the second wedge 5*b* slidably connect the wedge member 5 to the upper body portion 4 and/or to the lower body portion 6. In still another embodiment, a first set of dovetail grooves on the nose member 1 fix the nose member 1 to the upper body portion 4 and the lower body portion 6, and a second set of dovetail grooves on the wedge member 5 fix the upper body portion 4 and the lower body portion 6 to the wedge member 5.

Figure 6:
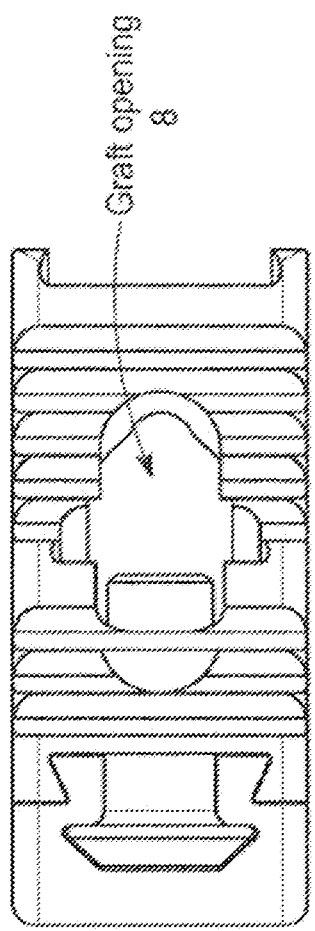
FIG. 6 is a schematic depicting a graft window in the implant.

FIG. 6 is a schematic depicting a bone graft window 8 in implant 20. As shown in FIG. 6, an opening in at least one of the upper body portion 4 and the lower body portion 6 is provided for bone graft window 8. The graft window is also incorporated into wedge member 5. In one embodiment of the invention, by disposing the actuator mechanism toward the nose of the implant 20, a relatively large graft window 8 is provided for the implant, and graft material can be injected into the implant 20 once inserted and expanded in the patient. The relatively large graft window facilitates the bone growth and fusion process. In one embodiment, the graft opening can range from 25% to 60% of the endplate area (e.g., the area of the upper or lower body portion) depending on the footprint of implant 20. Regardless of the opening size and configuration, in one embodiment, the implant device provides the capability to backfill bone graft material into a graft window passing all the way though the implant 20.

Figure 7:
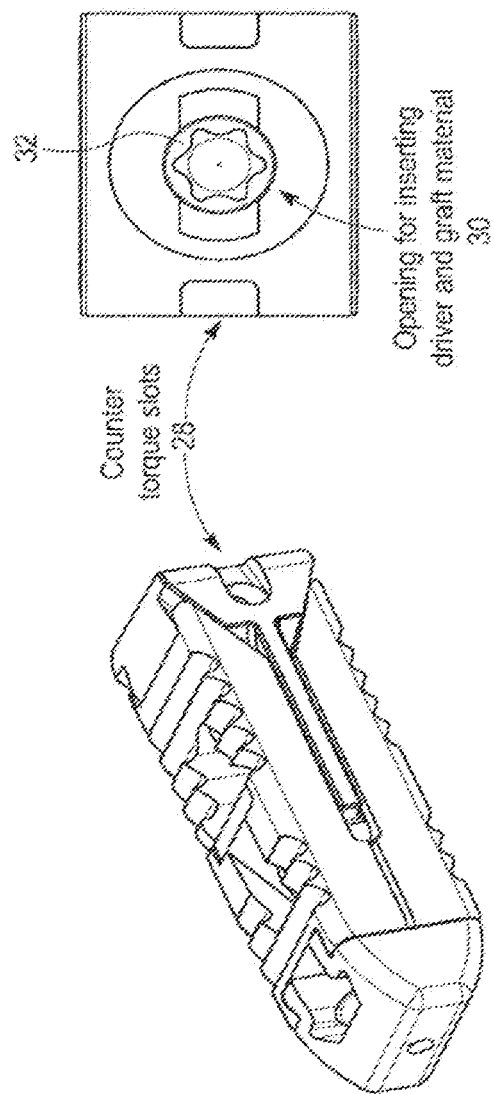
FIG. 7 is a schematic depicting counter torque slots of the implant.

FIG. 7 is a schematic depicting counter torque slots 28 of implant 20 and a through hole 30 in the posterior end of implant 20. The counter torque slots 28 permit an entirety of implant 20 to be rotated, that is implant 20 as a unit is rotatable. The counter torque slots 28 prevent the implant from rotating, or tipping over, during expansion. The counter torque slots 28 stabilize the implant 20 against the torque being applied to the actuator during expansion. The through-hole 30 grants access for the driver to the actuator. The through-hole 30 also represents an opening for the insertion of bone graft material. In one embodiment of the invention, the wedge member 5 comprises a first wedge 5a and a second wedge 5b connected together by a pair of rails 5c. A through-hole in the first wedge 5a, a second through-hole in the second wedge 5b, and a spacing between the rails 5c comprise a passageway for an insertion tool to connect to and turn actuator 3, and a passageway for bone graft material insertion.

In one embodiment of the invention, there is provided a system for stabilization of vertebra. This system utilizes any of the expandable implants described above; and an insertion tool which turns the actuator described above and thereby expands the implant. For example, actuator 3 shown above can be rotated by a T-7 hexalobular driver fitting the corresponding nut head 32 shown in FIG. 7. Accordingly, in one embodiment, the insertion tool engages the counter torque slots to 1) provide a counter torque during expansion and 2) retain the implant 20 to an inserter supplying bone graft material during the procedure. The bone graft inserter can be cannulated. In one embodiment, the above-noted T-7 driver is placed through the center of the bone graft inserter and engages the actuator. Bone graft material is then pushed through the inserter into implant 20 after implant 20 has been expanded.

In another embodiment of the invention, as shown in FIGS. 8A-1, 8A-2, 8A-3, and 8B, there is provided an expandable (intervertebral) implant comprising an upper body portion 4, a lower body portion 6 opposite the upper body portion 4, a wedge member 5 extending along a longitudinal axis of the implant 20 and connecting the upper body portion 4 to the lower body portion 6, a nose member 1 having a tapered distal end and a proximal end opposite the distal end, the nose member 1 slidably connected to the upper body portion 4 and the lower body portion 6, an actuator 3 disposed offset from the longitudinal axis and disposed between the nose member 1 and the wedge member 5, for translation of the wedge 5 member along a longitudinal axis of the implant, the actuator 3 on a first side slidably connected the nose member 1 and on a second side threadably connected to the wedge member 5, and a pin 2 connecting to the actuator 3.

Figures 1, 8A:
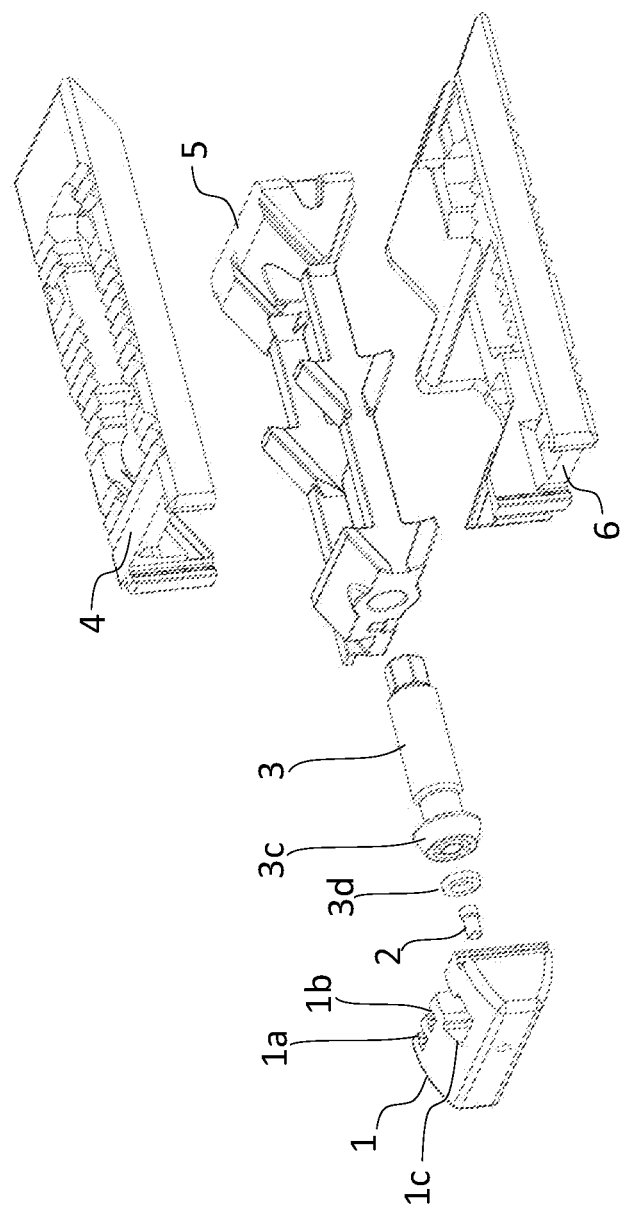
Figures 2, 8A:
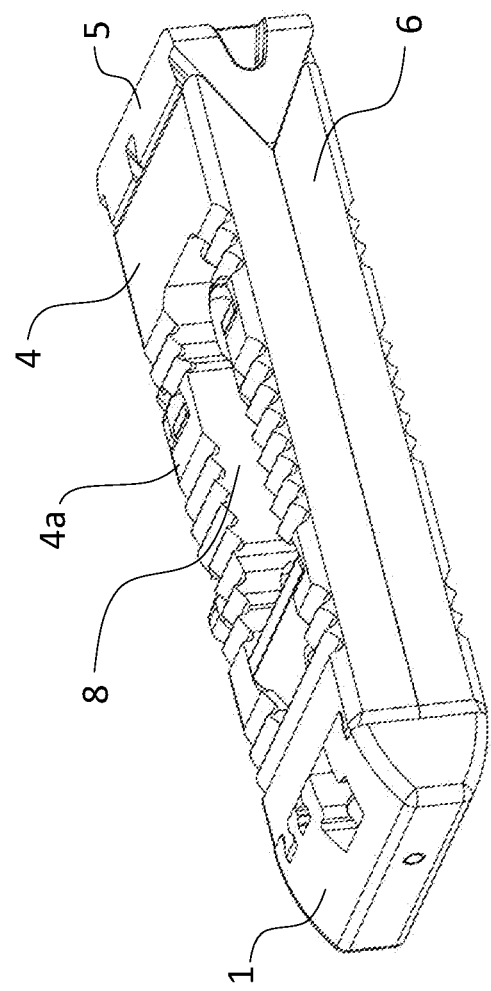
Figures 3, 8A:
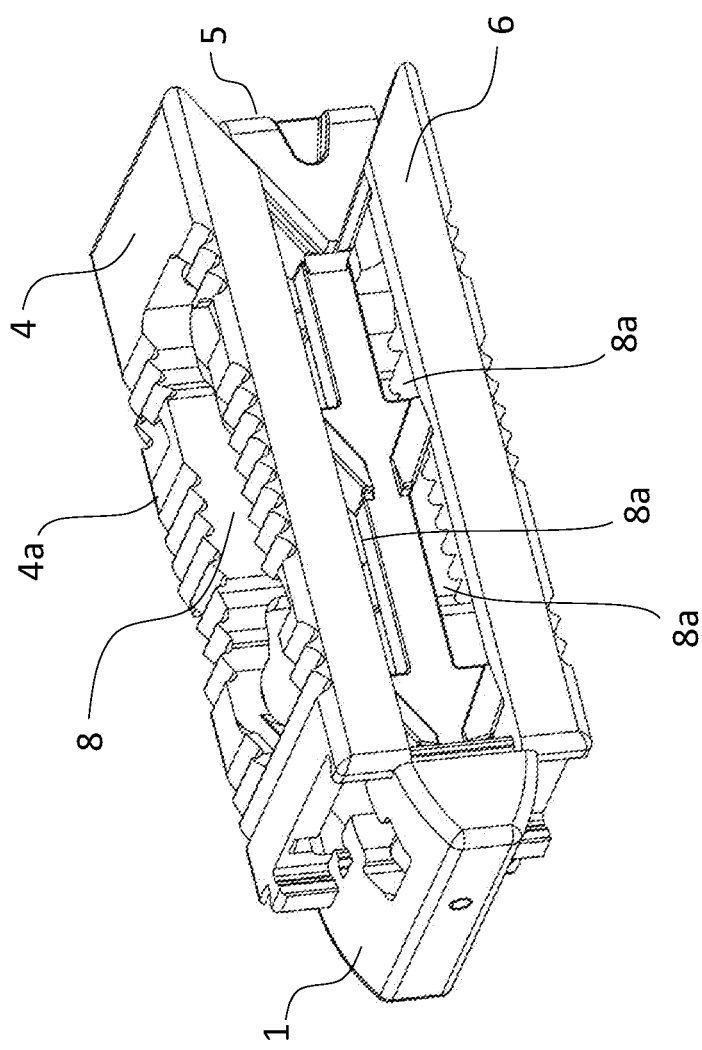

FIGS. 8A-2, and 8A-3 show respectively the collapsed and expanded states of the expandable implant. In the expanded state, there are both the graft window 8 and openings 8a along the lateral sides of the implant for the supply of graft material throughout the internal volume of the implant.

Figure 8B:
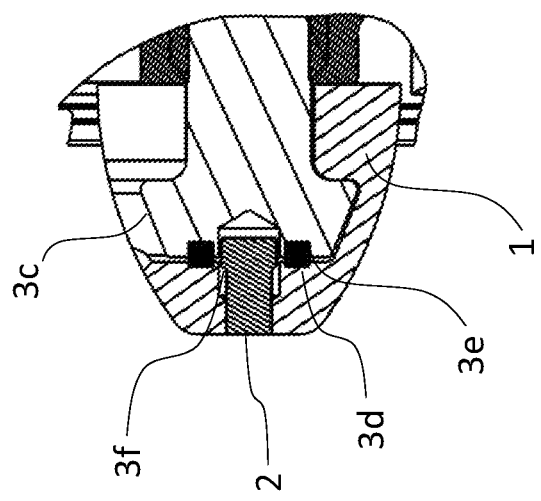
FIG. 8B is an expanded view of the head of the actuator for the implant shown in FIG. 8A.

Optionally, as shown in the expanded view of FIG. 8B, toward the first side of the actuator 3, the actuator 3 has a flange 3c, a reception hole 3f in the flange 3c disposed on a central axis of the actuator 3 for reception of pin 2, and a washer 3d disposed on the flange (e.g., in recess 3e) and surrounding the reception hole 3f. Translation of the wedge member 5 along the longitudinal axis of the implant 20 displaces the upper body portion 4 and the lower body portion 6 away from each other, thereby expanding the intervertebral implant 20. When washer 3d is present and due to a relatively tight tolerance (with a thickness washer 3d exceeding slightly the thickness of the recess 3c), washer 3d is compressed as the nose member 1 and the actuator 3 are assembled together. In this embodiment, as before, washer 3d in the compressed state comprises the aforementioned frictional bearing.

Figure 8C:
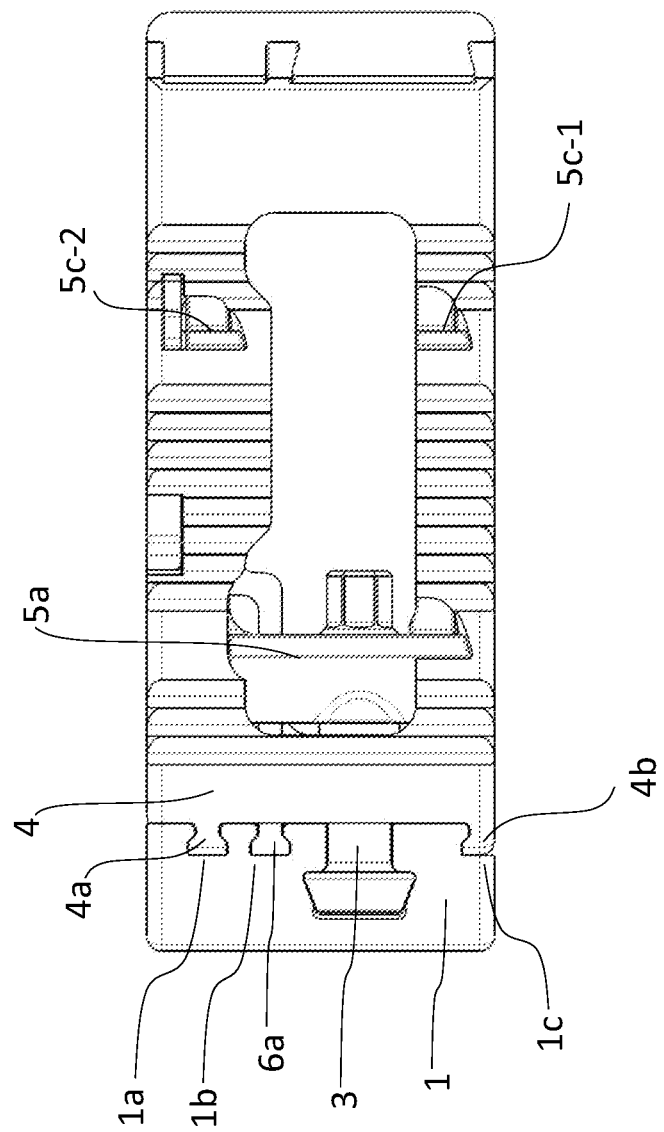
FIG. 8C is a schematic depiction of another aspect of the implant shown in FIG. 8A.

In one embodiment of the invention, as shown in FIG. 8C, there is provided an expandable intervertebral implant having an asymmetric graft window 8 with a larger opening to an anterior side of the implant than to a posterior side of the implant 20. Since the designation of anterior and posterior relates to a preferred direction for insertion into the patient, in general, there is provided an expandable intervertebral implant having an asymmetric graft window 8 with a larger opening to one side of the implant than to another, opposing side of implant 20. In general, the terms superior, inferior, posterior, and anterior as used herein may refer to the orientation of the expandable implant as it is inserted between vertebrae. However, the invention is not so limited and these terms also define merely the relative orientation of the sides of the expandable implant to one another. For example, the superior and inferior terms refer to opposing sides to the implant for connection to the vertebrae, the opposing members on those sides expanding relative to each other. For example, the posterior and anterior terms refer to opposing sides to the implant which are positioned laterally across from each other, and in general transverse to the longitudinal axis of the implant.

While the asymmetric graft window 8 depicted in FIG. 8C is shown with the offset actuator of FIG. 8A, the present invention is not so limited, and the asymmetric graft window 8 can be used with the expandable implant shown in FIGS. 1 and 2 where either or both of the upper body portion 4 and the lower body portion 6 shown in FIGS. 1 and 2 have an asymmetric graft window 8.

In one embodiment, as shown in FIG. 8C, on a side of the implant opposite the off-axis actuator 3, a pair of dovetail grooves 1a, 1b on nose member 1 engages dovetails 4a, 6a disposed respectively on the upper body portion 4 and the lower body portion 6 to hold and slidably connect the upper body portion 4 and the lower body portion 6 to the nose member 1. Also, shown in FIG. 8C is the common dovetail groove 1c on the anterior side of nose member 1 which engages with dovetail 4b on the upper body portion 4 and dovetail 6b on the lower body portion 6.

Figure 8D:
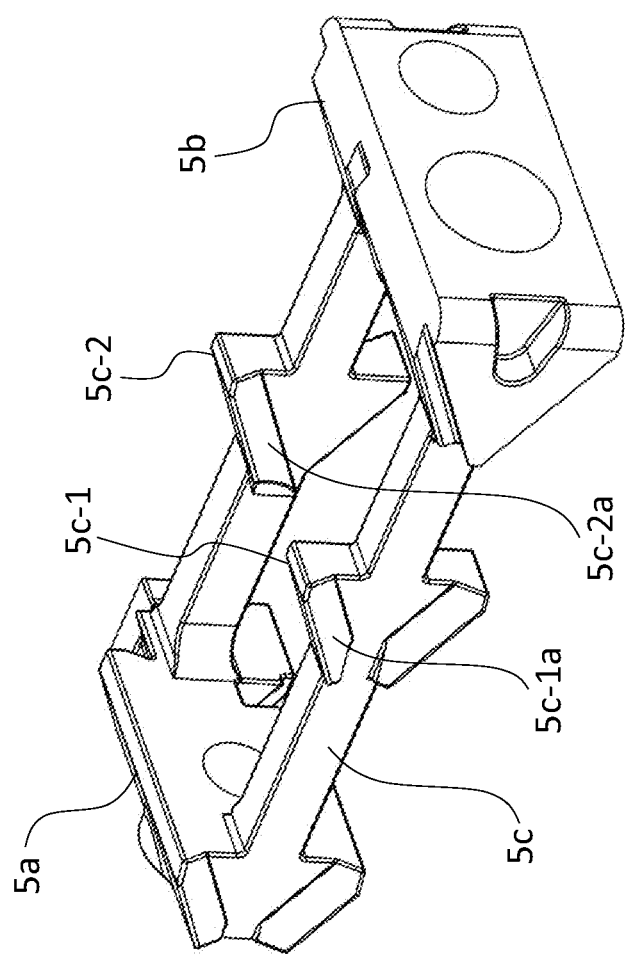
FIG. 8D is a schematic depiction of another aspect of the implant shown in FIG. 8A.

In one embodiment, as shown in FIG. 8D, wedge member 5 comprises in order a first wedge 5a, a pair of second (middle) wedges 5c-1 and 5c-2, and a third wedge 5b connected together by a rail 5c. That is the wedge member 5 comprises a leading wedge 5a, an intermediate wedge 5c-1 and 5c-2, and a trailing wedge 5b. The pair of second (middle) wedges 5c-1 and 5c-2 are spaced apart from each other to provide more clearance for the graft window 8, 22. In one embodiment, the pair of wedges 5c-1 and 5c-2 comprises an anterior wedge 5c-1 and a posterior wedge 5c-2 with the anterior wedge 5c-1 has an anterior dovetail groove disposed outside the graft window 8 and with the posterior wedge 5c-2 having a posterior dovetail groove 5c-2a disposed in the graft window 8.

Figures 1, 8E:
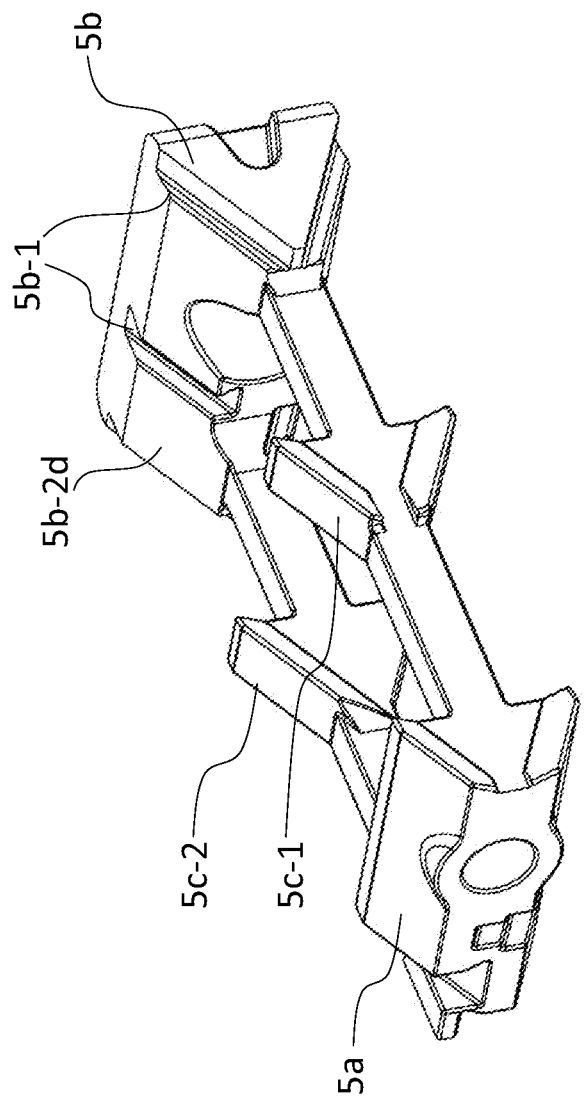
Figures 2, 8E:
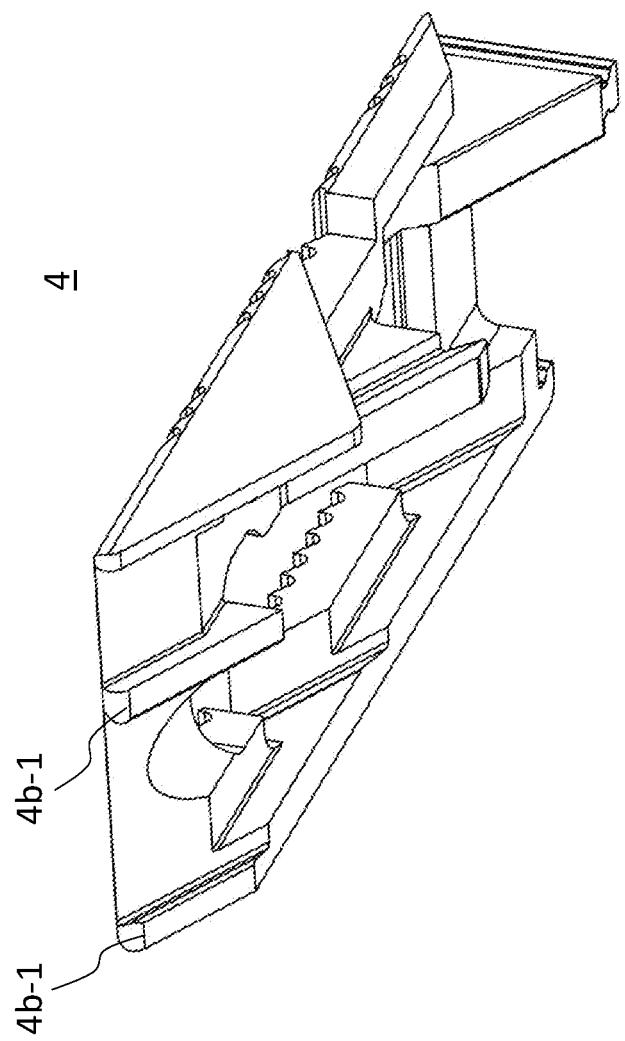

As illustrated in FIG. 8E-1, wedge 5b contains dovetail grooves 5b-1 extending in this example along an entire length of the inclined surface 5b-2 of wedge 5b. Complementary dovetails on the upper body portion 4 slide into the dovetail groves 5b-1.

As illustrated in FIG. 8E-2, the upper body portion 4 has dovetails 4b-1 which slide in dovetail grooves 5b-1 on wedge member 5.

In one embodiment, posterior wedge 5c-2 is shorter in height than anterior wedge 5c-1. The relative heights of posterior wedge 5c-2 and anterior wedge 5c-1 define a lordotic angle for the implant tapering downward toward a posterior side of the implant. Further, as seen in FIGS. 8D and 8E-1, anterior wedge 5c-1 has a) an upper half with a superior dovetail 5c-1a disposed outside the graft window and b) a lower half with an inferior dovetail disposed outside the graft window. Also, as seen in FIGS. 8D and 8E-1, posterior wedge 5c-2 has a) an upper half with a superior dovetail 5c-2a disposed inside the graft window and b) a lower half with an inferior dovetail groove disposed outside the graft window.

Figure 8F:
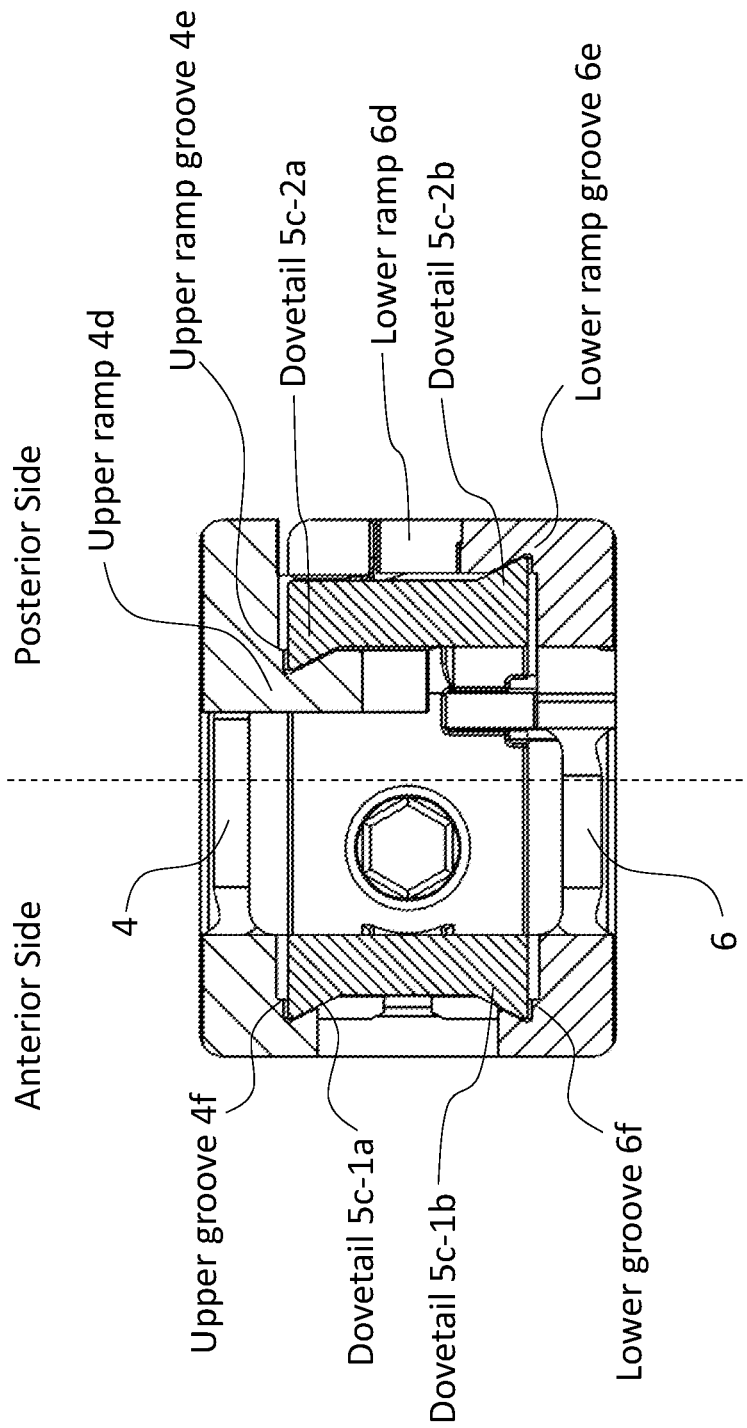
FIG. 8F is a schematic depiction of another aspect of the implant shown in FIG. 8A

FIG. 8F is a schematic of an end view of an expanded state of the expandable implant shown in FIG. 8A-3. As seen FIG. 8F, in the expanded state on a posterior side of the implant, an upper ramp 4d extending downward from the upper body portion 4 partially overlaps a lower ramp 6d extending upward from the lower body portion 6. In the collapsed state, the overlap is even more complete. Also, an upper dovetail groove 4e in the upper ramp 4d on the posterior side engages the superior dovetail 5c-2a inside the graft window and a lower dovetail groove 6e in the lower ramp 6d on the posterior side engages the inferior dovetail 5c-2b that is disposed outside the graft window. On the anterior side, dovetail grooves 4f, 6f in respectively the upper and lower plates 4, 6 engage the dovetails 5c-1a, 5c-1b outside the graft window.

The expandable implants of the present invention are not limited to the type of material that the implant is made of. The implants of this invention can be made of any material appropriate for human implantation and having the mechanical properties sufficient to be utilized for the intended purpose of spinal fusion, including various metals such as cobalt chrome, stainless steel or titanium including its alloys, various plastics including those which are bioabsorbable, and various ceramics or combination sufficient for the intended purpose. Further, the implants of this invention may be made of a solid material, a mesh-like material, a porous material and may comprise, wholly or in part, materials capable of directly participating in the spinal fusion process, or be loaded with, composed of, treated of coated with chemical substances such as bone, morphogenic proteins, hydroxyapatite in any of its forms, and osteogenic proteins, to make them bioactive for the purpose of stimulating spinal fusion. The implants of this invention may be wholly or in part bioabsorbable. Other materials for the implant device besides those specifically listed above can be used.

This invention is also not limited to the methods by which the implants are made. The individual components can be machined from solid stock pieces. Molding can be used to make the individual components. In this case, machining to final dimensions may or may not be in order. The surfaces once properly dimensioned can be coated with a variety of biocompatible coatings and/or surface treatments. Various coatings include for example calcium phosphate ceramics, such as tricalcium phosphate (TCP) and hydroxyapatite (HA), and hydroxyapatite (a naturally occurring material in bone). Moreover. If the implant is not made of bone, surfaces of the implant that contact bone may be treated to promote fusion of the implant to the bone. Treatment may include, but is not limited to, applying a hydroxyapatite coating on contact surfaces, spraying a titanium plasma on contact surfaces, and/or texturing the contact surfaces by scoring, peening, implanting particles in the surfaces, or otherwise roughening the surfaces of the implant.

Operation of Expandable Implants

Figure 9:
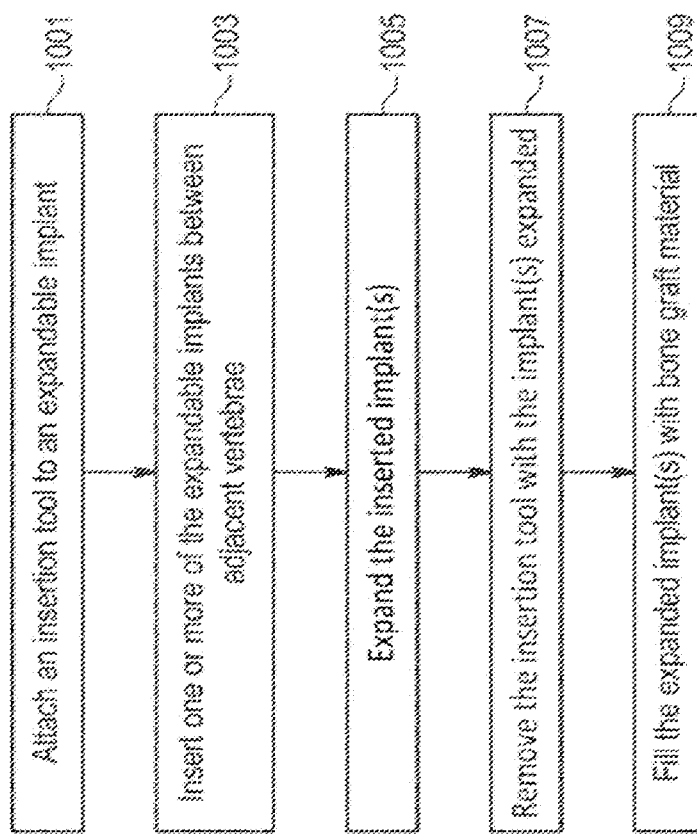
FIG. 9 is a flowchart depicting a method of the invention for stabilization of vertebra.

In one embodiment of the invention, there is provided a method for stabilization of vertebra. FIG. 9 is a flowchart depicting this method. This method at 1001 attaches an insertion tool to any of the expandable implants described above. At 1003, the method inserts one (or more) of the expandable implants into an intervertebral space between adjacent vertebrae; and at 1005 expands the expandable implant.

After the expandable implant has been expanded, at 1007, the insertion tool may be removed (e.g., may be pulled from through hole 30 in the posterior end of implant 20. At 1009, bone graft material may then be inserted into the expanded implant filling the graft window 8 in situ. As noted above, the insertion of bone graft material promotes increased fusion.

This invention is not limited to a specific type of bone graft material. In general, a variety of bone graft materials are known and suitable for this invention. These typically comprise calcium phosphate-based or gel-based materials. Polymer-based bone graft substitutes containing (or not containing) collagen can be used. Ceramic bone graft substitutes can be used. In one embodiment, the implantable bone graft material comprises a composite of a ceramic and a polymer. The ceramic and the polymer can be present at a weight ratio ranging from about 10:1 ceramic to polymer to about 2:1 ceramic to polymer. Alternatively, the weight ratio of the ceramic to the polymer can range from about 2:1 (about 66% ceramic to about 33% polymer), from about 3:1 (about 75% ceramic to about 25% polymer), from about 4:1 (about 80% ceramic to about 20% polymer), from about 9:1 (about 90% ceramic to about 10% polymer), from about 10:1 (about 99% ceramic to about 1% polymer). Other bone graft materials besides those specifically listed above can be used.

In some embodiments, any of the implants and instruments described above (such as the insertion tool) can be used with additional implants and instruments. In some embodiments, the implants and instruments can be used with stabilization members, such as plates, screws, and rods. In addition, a multi-level construct can be formed, wherein any one or more of the implants 20 described above can be used on one level, while a similar or different implant (e.g., fusion or prosthetic) can be used on a different level.

STATEMENTS OF THE INVENTION

The following statements of the invention represent various aspects of the invention.

Statement 1. An expandable intervertebral implant comprising:

an upper body portion;

a lower body portion opposite the upper body portion;

a wedge member connecting the upper body portion to the lower body portion;

a nose member having a tapered distal end and a proximal end opposite the distal end, the nose member slidably connected to the upper body portion and the lower body portion;

an actuator disposed between the nose member and the wedge member for translation of the wedge member toward the nose member;

the actuator on a first side slidably connected the nose member and on a second side threadably connected to the wedge member;

a pin connects to the actuator for positioning the nose member relative to the actuator; and a frictional bearing contacting the actuator and providing a frictional force retarding movement of the upper body portion relative to the lower body portion, wherein translation of the wedge member along the longitudinal axis of the implant displaces the upper body portion and the lower body portion away from each other, thereby expanding the intervertebral implant.

Statement 2. The implant of statement 1, further comprising:
a flange,
a reception hole in the flange disposed on a central axis of the actuator for reception of
the pin, and
a washer disposed on the flange and surrounding the reception hole,
wherein the washer comprises the frictional bearing held in a compressed state between the actuator and the nose member, thereby providing the frictional force retarding movement of the upper body portion relative to the lower body portion.

Statement 3. The implant of any statement above, further comprising an opening in at least one of the upper body portion and the lower body portion for a bone graft window.

Statement 4. The implant of any statement above, wherein at least one of the upper body portion and the lower body portion comprises a corrugated surface.

Statement 5. The implant of any statement above, wherein the actuator is threadably connected to the wedge member such that rotating the actuator translates the wedge member along toward the nose member.

Statement 6. The implant of any statement above, wherein dovetails on the wedge member hold and slidably connect the upper body portion and the lower body portion to the wedge member.

Statement 7. The implant of any statement above, wherein dovetail grooves on the nose member hold and slidably connect the upper body portion and the lower body portion to the nose member.

Statement 8. The implant of any statement above, wherein a drive end of the actuator opposite the nose member is configured to connect with an insertion tool for insertion of the implant between vertebrae.

Statement 9. The implant of any statement above, wherein a head of the actuator, opposite the wedge member, is located in the nose member.

Statement 10. The implant of any statement above, wherein the actuator by turning advances the wedge member toward the nose member to expand the implant, and the actuator and the wedge member have respectively male and female threads to thereby advance the wedge member when the actuator is turned.

Statement 11. The implant of any statement above, wherein the pin maintains a position of the nose member relative to the actuator once the implant has been assembled, the position being offset from a longitudinal axis of the wedge member.

Statement 12. The implant of any statement above, wherein, on a posterior side of the implant, plural dovetail grooves in the nose member respectively hold and slidably connect the upper body portion and the lower body portion to the nose member.

Statement 13. The implant of statement 12, wherein, on an anterior side of the implant, a common dovetail groove in the endplate holds and slidably connects the upper body portion and the lower body portion to the nose member.

Statement 14. The implant of any statement above, wherein a through-hole in the wedge member comprises a passageway for an insertion tool to connect to and turn the actuator.

Statement 15. The implant of any statement above, wherein the wedge member comprises a leading wedge, an intermediate wedge, and a trailing wedge connected together by a pair of rails, and the intermediate wedge comprises a pair of wedges with a gap in between.

Statement 16. The implant of any statement above, wherein a posterior wedge of the pair of wedges is shorter in height than an anterior wedge of the pair of wedges, relative heights of the posterior wedge and the anterior wedge defining a lordotic angle tapering downward toward a posterior side of the implant.

Statement 17. The implant of statement 16, wherein the anterior wedge has a) an upper half with a superior dovetail disposed outside the graft window and b) a lower half with an inferior dovetail disposed outside the graft window.

Statement 18. The implant of statement 16, wherein the posterior wedge has a) an upper half with a superior dovetail disposed inside the graft window and b) a lower half with an inferior dovetail groove disposed outside the graft window.

Statement 19. The implant of statement 18, wherein,
in a collapsed state on a posterior side of the implant, an upper ramp extending downward from the upper body portion overlaps a lower ramp extending upward from the lower body portion, and
an upper dovetail groove in the upper ramp on the posterior side engages the superior dovetail inside the graft window and a lower dovetail groove in the lower ramp on the posterior side engages the inferior dovetail that is disposed outside the graft window.

Statement 20. The implant of any statement above, wherein, on an anterior side of the nose member, a dovetail groove comprises a slot to receive therein a head of the actuator.

Statement 21. The implant of any statement above, wherein the wedge member extends along a longitudinal axis of the implant, and the actuator is disposed offset from the longitudinal axis.

Statement 22. The implant of any statement above, wherein at least one of the upper body portion and the lower body portion has an asymmetric graft window with a larger opening to a first side of the implant extending along a length of the wedge member than to a second side of the implant opposite the first side.

Statement 23. The implant of any statement above, wherein at least one of the upper body portion and the lower body portion has an asymmetric graft window with a larger opening to an anterior side of the implant than to a posterior side of the implant.

Statement 24. An expandable intervertebral implant comprising:
an upper body portion;
a lower body portion opposite the upper body portion;
a wedge member extending along a longitudinal axis of the implant and connecting the upper body portion to the lower body portion;
a nose member having a tapered distal end and a proximal end opposite the distal end, the nose member slidably connected to the upper body portion and the lower body portion;
an actuator disposed offset from the longitudinal axis of the wedge member and disposed between the nose member and the wedge member for translation of the wedge member along a longitudinal axis of the implant;
the actuator on a first side slidably connected the nose member and on a second side connected to the wedge member;
a pin connects to the actuator for positioning the nose member relative to the actuator; and
wherein
translation of the wedge member along the longitudinal axis of the implant displaces the upper body portion and the lower body portion away from each other, thereby expanding the intervertebral implant.

Statement 25. The implant of statement 24, further comprising a frictional bearing providing a frictional force retarding movement of the upper body portion relative to the lower body portion.

Statement 26. The implant of statement 24 and any statements after statement 24, further comprising an opening in at least one of the upper body portion and the lower body portion for a bone graft window.

Statement 27. The implant of statement 24 and any statements after statement 24, wherein at least one of the upper body portion and the lower body portion comprises a corrugated surface.

Statement 28. The implant of statement 24 and any statements after statement 24, wherein the actuator is threadably connected to the wedge member such that rotating the actuator translates the wedge member along toward the nose member.

Statement 29. The implant of statement 24 and any statements after statement 24, wherein dovetails on the wedge member hold and slidably connect the upper body portion and the lower body portion to the wedge member.

Statement 30. The implant of statement 24 and any statements after statement 24, wherein dovetail grooves on the nose member hold and slidably connect the upper body portion and the lower body portion to the nose member.

Statement 31. The implant of statement 24 and any statements after statement 24, wherein a drive end of the actuator opposite the nose member is configured to connect with an insertion tool for insertion of the implant between vertebrae.

Statement 32. The implant of statement 24 and any statements after statement 24, wherein a head of the actuator, opposite the wedge member, is located in the nose member.

Statement 33. The implant of statement 24 and any statements after statement 24, wherein the actuator by turning advances the wedge member toward the nose member to expand the implant, and the actuator and the wedge member have respectively male and female threads to thereby advance the wedge member when the actuator is turned.

Statement 34. The implant of statement 24 and any statements after statement 24, wherein the pin maintains a position of the nose member relative to the actuator once the implant has been assembled, the position being offset from a longitudinal axis of the wedge member.

Statement 35. The implant of statement 24 and any statements after statement 24, wherein, on a posterior side of the implant, plural dovetail grooves in the nose member respectively hold and slidably connect the upper body portion and the lower body portion to the nose member.

Statement 36. The implant of statement 35, wherein, on an anterior side of the implant, a common dovetail groove in the endplate holds and slidably connects the upper body portion and the lower body portion to the nose member.

Statement 37. The implant of statement 24 and any statements after statement 24, wherein a through-hole in the wedge member comprises a passageway for an insertion tool to connect to and turn the actuator.

Statement 38. The implant of statement 24 and any statements after statement 24, wherein the wedge member comprises a leading wedge, an intermediate wedge, and a trailing wedge connected together by a pair of rails, and the intermediate wedge comprises a pair of wedges with a gap in between.

Statement 39. The implant of statement 24 and any statements after statement 24, wherein a posterior wedge of the pair of wedges is shorter in height than an anterior wedge of the pair of wedges, relative heights of the posterior wedge and the anterior wedge defining a lordotic angle tapering downward toward a posterior side of the implant.

Statement 40. The implant of statement 39, wherein the anterior wedge has a) an upper half with a superior dovetail disposed outside the graft window and b) a lower half with an inferior dovetail disposed outside the graft window.

Statement 41. The implant of statement 39, wherein the posterior wedge has a) an upper half with a superior dovetail disposed inside the graft window and b) a lower half with an inferior dovetail groove disposed outside the graft window.

Statement 42. The implant of statement 41, wherein, in a collapsed state on a posterior side of the implant, an upper ramp extending downward from the upper body portion overlaps a lower ramp extending upward from the lower body portion, and an upper dovetail groove in the upper ramp on the posterior side engages the superior dovetail inside the graft window and a lower dovetail groove in the lower ramp on the posterior side engages the inferior dovetail that is disposed outside the graft window.

Statement 43. The implant of statement 24 and any statements after statement 24, wherein, on an anterior side of the nose member, a dovetail groove comprises a slot to receive therein a head of the actuator.

Statement 44. The implant of statement 24 and any statements after statement 24 wherein at least one of the upper body portion and the lower body portion has an asymmetric graft window with a larger opening to a first side of the implant extending along a length of the wedge member than to a second side of the implant opposite the first side.

Statement 45. The implant of statement 24 and any statements after statement 24, wherein at least one of the upper body portion and the lower body portion has an asymmetric graft window with a larger opening to an anterior side of the implant than to a posterior side of the implant.

Statement 46. An expandable intervertebral implant comprising:

an upper body portion having an asymmetric graft window with a larger opening to an anterior side of the implant than to a posterior side of the implant;

a lower body portion opposite the upper body portion;

a wedge member connecting the upper body portion to the lower body portion, the wedge member comprises in order a first wedge, a second wedge, and a third wedge connected together by a rail, the second wedge comprising a posterior wedge and an anterior wedge separated from the posterior wedge, wherein the posterior wedge occludes the graft window on the posterior side of the implant;

a nose member having a tapered distal end and a proximal end opposite the distal end, the nose member slidably connected to the upper body portion and the lower body portion;

an actuator disposed between the nose member and the wedge member for translation of the wedge member along a longitudinal axis of the implant;

the actuator on a first side slidably connected the nose member and on a second side connected to the wedge member;

a pin connects to the actuator for positioning the nose member relative to the actuator; and wherein translation of the wedge member along the longitudinal axis of the implant displaces the upper body portion and the lower body portion away from each other, thereby expanding the intervertebral implant.

Statement 47. The implant of statement 46, further comprising a frictional bearing providing a frictional force retarding movement of the upper body portion relative to the lower body portion.

Statement 48. The implant of statement 46 and any statements after statement 46, further comprising an opening in at least one of the upper body portion and the lower body portion for a bone graft window.

Statement 49. The implant of statement 46 and any statements after statement 46, wherein at least one of the upper body portion and the lower body portion comprises a corrugated surface.

Statement 50. The implant of statement 46 and any statements after statement 46, wherein the actuator is threadably connected to the wedge member such that rotating the actuator translates the wedge member along toward the nose member.

Statement 51. The implant of statement 46 and any statements after statement 46, wherein dovetails on the wedge member hold and slidably connect the upper body portion and the lower body portion to the wedge member.

Statement 52. The implant of statement 46 and any statements after statement 46, wherein dovetail grooves on the nose member hold and slidably connect the upper body portion and the lower body portion to the nose member.

Statement 53. The implant of statement 46 and any statements after statement 46, wherein a drive end of the actuator opposite the nose member is configured to connect with an insertion tool for insertion of the implant between vertebrae.

Statement 54. The implant of statement 46 and any statements after statement 46, wherein a head of the actuator, opposite the wedge member, is located in the nose member.

Statement 55. The implant of statement 46 and any statements after statement 46, wherein the actuator by turning advances the wedge member toward the nose member to expand the implant, and the actuator and the wedge member have respectively male and female threads to thereby advance the wedge member when the actuator is turned.

Statement 56. The implant of statement 46 and any statements after statement 46, wherein the pin maintains a position of the nose member relative to the actuator once the implant has been assembled, the position being offset from a longitudinal axis of the wedge member.

Statement 57. The implant of statement 46 and any statements after statement 46, wherein, on a posterior side of the implant, plural dovetail grooves in the nose member respectively hold and slidably connect the upper body portion and the lower body portion to the nose member.

Statement 58. The implant of statement 57, wherein, on an anterior side of the implant, a common dovetail groove in the endplate holds and slidably connects the upper body portion and the lower body portion to the nose member.

Statement 59. The implant of statement 46 and any statements after statement 46, wherein a through-hole in the wedge member comprises a passageway for an insertion tool to connect to and turn the actuator.

Statement 60. The implant of statement 46 and any statements after statement 46, wherein the second wedge comprises a pair of wedges with a gap in between.

Statement 61. The implant of statement 46 and any statements after statement 46, wherein relative heights of the posterior wedge and the anterior wedge define a lordotic angle tapering downward toward a posterior side of the implant.

Statement 62. The implant of statement 46 and any statements after statement 46, wherein the anterior wedge has a) an upper half with a superior dovetail disposed outside the graft window and b) a lower half with an inferior dovetail disposed outside the graft window.

Statement 63. The implant of statement 46 and any statements after statement 46, wherein the posterior wedge has a) an upper half with a superior dovetail disposed inside the graft window and b) a lower half with an inferior dovetail groove disposed outside the graft window.

Statement 64. The implant of statement 63, wherein, in a collapsed state on a posterior side of the implant, an upper ramp extending downward from the upper body portion overlaps a lower ramp extending upward from the lower body portion, and an upper dovetail groove in the upper ramp on the posterior side engages the superior dovetail inside the graft window and a lower dovetail groove in the lower ramp on the posterior side engages the inferior dovetail that is disposed outside the graft window.

Statement 65. The implant of statement 46 and any statements after statement 46, wherein, on an anterior side of the nose member, a dovetail groove comprises a slot to receive therein a head of the actuator.

Statement 66. An expandable intervertebral implant comprising:

an upper body portion having an asymmetric graft window with a larger opening to an anterior side of the implant than to a posterior side of the implant;

a lower body portion opposite the upper body portion;

a wedge member connecting the upper body portion to the lower body portion.

a nose member having a tapered distal end and a proximal end opposite the distal end, the nose member slidably connected to the upper body portion and the lower body portion;

an actuator disposed between the nose member and the wedge member for translation of the wedge member along a longitudinal axis of the implant;

the actuator on a first side slidably connected the nose member and on a second side connected to the wedge member;

a pin connects to the actuator for positioning the nose member relative to the actuator; and wherein translation of the wedge member along the longitudinal axis of the implant displaces the upper body portion and the lower body portion away from each other, thereby expanding the intervertebral implant.

Numerous modifications and variations of the present invention are possible in light of the above teachings. It is therefore to be understood that within the scope of the appended claims, the invention may be practiced otherwise than as specifically described herein.

The invention claimed is:

1. An expandable intervertebral implant comprising:
   an upper body portion;
   a lower body portion opposite the upper body portion;
   a wedge member connecting the upper body portion to the lower body portion;
   a nose member having a tapered distal end and a proximal end opposite the distal end, the nose member slidably connected to the upper body portion and the lower body portion;
   an actuator disposed between the nose member and the wedge member for translation of the wedge member toward the nose member;
   the actuator on a first side slidably connected to the nose member and on a second side threadably connected to the wedge member;
   a pin connected to the actuator for positioning the nose member relative to the actuator; and
   a compressible frictional bearing contacting the actuator and, when the compressible frictional bearing is compressed against the actuator, providing a frictional force retarding movement of the upper body portion relative to the lower body,
   wherein
   translation of the wedge member along a longitudinal axis of the implant displaces the upper body portion and the lower body portion away from each other, thereby expanding the implant.

2. The implant of claim 1, wherein the actuator comprises:
   a flange,
   a reception hole in the flange disposed on a central axis of the actuator for reception of the pin, and
   a washer disposed on the flange and surrounding the reception hole,
   wherein the washer comprises the compressible frictional bearing held in a compressed state between the actuator and the nose member, thereby providing the frictional force retarding movement of the upper body portion relative to the lower body portion.

3. The implant of claim 1, further comprising a bone graft window opening in at least one of the upper body portion and the lower body portion.

4. The implant of claim 1, wherein dovetails on the wedge member hold and slidably connect the upper body portion and the lower body portion to the wedge member.

5. The implant of claim 1, wherein dovetail grooves on the nose member hold and slidably connect the upper body portion and the lower body portion to the nose member.

6. The implant of claim 1, wherein a head of the actuator, opposite the wedge member, is located in the nose member.

7. The implant of claim 1,
   wherein the actuator by turning advances the wedge member toward the nose member to expand the implant, and
   wherein the actuator and the wedge member have threads to thereby advance the wedge member when the actuator is turned.

8. The implant of claim 1, wherein the pin maintains a position of the nose member relative to the actuator once the implant has been assembled, the position being offset from a longitudinal axis of the wedge member.

9. The implant of claim 1, wherein, on a posterior side of the implant, plural dovetail grooves in the nose member respectively hold and slidably connect the upper body portion and the lower body portion to the nose member.

10. The implant of claim 9, wherein, on an anterior side of the implant, a dovetail groove in the wedge member holds and slidably connects the upper body portion and the lower body portion to the nose member.

11. The implant of claim 1, wherein
   a through-hole in the wedge member comprises a passageway for an insertion tool to connect to and turn the actuator.

12. The implant of claim 1,
   wherein the wedge member comprises a leading wedge, an intermediate wedge, and a trailing wedge connected together by a pair of rails, and
   wherein the intermediate wedge comprises a pair of wedges with a gap in between.

13. The implant of claim 12, wherein a posterior wedge of the pair of wedges is shorter in height than an anterior wedge of the pair of wedges, relative heights of the posterior wedge and the anterior wedge defining a lordotic angle tapering downward toward a posterior side of the implant.

14. The implant of claim 13, wherein the anterior wedge has a) an upper half with a superior dovetail disposed outside a bone graft window and b) a lower half with an inferior dovetail disposed outside the bone graft window.

15. The implant of claim 13, wherein the posterior wedge has a) an upper half with a superior dovetail disposed inside a bone graft window and b) a lower half with an inferior dovetail groove disposed outside the bone graft window.

16. The implant of claim 15, wherein,
   in a collapsed state on a posterior side of the implant, an upper ramp extending downward from the upper body portion overlaps a lower ramp extending upward from the lower body portion, and
   an upper dovetail groove in the upper ramp on the posterior side engages the superior dovetail inside the bone graft window and a lower dovetail groove in the lower ramp on the posterior side engages the inferior dovetail that is disposed outside the bone graft window.

17. The implant of claim 1, wherein, on an anterior side of the nose member, a dovetail groove comprises a slot to receive a head of the actuator therein.

18. An expandable intervertebral implant comprising:
   an upper body portion;
   a lower body portion opposite the upper body portion;
   a wedge member connecting the upper body portion to the lower body portion;
   a nose member having a tapered distal end and a proximal end opposite the distal end, the nose member slidably connected to the upper body portion and the lower body portion;
   an actuator disposed between the nose member and the wedge member for translation of the wedge member toward the nose member;
   the actuator on a first side slidably connected the nose member and on a second side threadably connecting to the wedge member;
   a pin connects to the actuator for positioning the nose member relative to the actuator; and
   a frictional bearing contacting the actuator and providing a frictional force retarding movement of the upper body portion relative to the lower body,
   wherein translation of the wedge member along a longitudinal axis of the implant displaces the upper body portion and the lower body portion away from each other, thereby expanding the implant, and
   wherein the wedge member extends along a longitudinal axis of the implant, and the actuator is disposed offset from the longitudinal axis.

19. The implant of claim 1, wherein at least one of the upper body portion and the lower body portion has an asymmetric bone graft window with a larger opening to a first side of the implant extending along a length of the wedge member than to a second side of the implant opposite the first side.

20. The implant of claim 1, wherein at least one of the upper body portion and the lower body portion has an asymmetric bone graft window with a larger opening to an anterior side of the implant than to a posterior side of the implant.

* * * * *